(12) United States Patent
Donohue et al.

(10) Patent No.: US 12,337,119 B2
(45) Date of Patent: Jun. 24, 2025

(54) METHODS AND SYSTEMS FOR INTERACTIVE DELIVERY OF DIGITAL CONTENT RESPONSIVE TO EMOTIONAL STATE

(71) Applicant: The Digital Wellness Center Inc., Toronto (CA)

(72) Inventors: Mary Donohue, Toronto (CA); Steve Demelo, Toronto (CA)

(73) Assignee: THE DIGITAL WELLNESS CENTER INC., Toronto (CA)

( * ) Notice: Subject to any disclaimer, the term of this patent is extended or adjusted under 35 U.S.C. 154(b) by 0 days.

(21) Appl. No.: 18/371,957

(22) Filed: Sep. 22, 2023

(65) Prior Publication Data

US 2024/0100294 A1    Mar. 28, 2024

Related U.S. Application Data

(60) Provisional application No. 63/408,956, filed on Sep. 22, 2022.

(51) Int. Cl.
| | |
|---|---|
| *A61M 21/02* | (2006.01) |
| *A61B 5/00* | (2006.01) |
| *A61B 5/16* | (2006.01) |
| *A61M 21/00* | (2006.01) |
| *G16H 20/70* | (2018.01) |

(52) U.S. Cl.
CPC .............. *A61M 21/02* (2013.01); *A61B 5/165* (2013.01); *A61B 5/4836* (2013.01); *G16H 20/70* (2018.01); *A61M 2021/0027* (2013.01); *A61M 2021/005* (2013.01)

(58) Field of Classification Search
CPC ........... A61B 5/16; A61B 5/165; A61B 5/486; A61B 5/4884; A61B 5/7264; G16H 10/20; G16H 50/20; G09B 5/00; G09B 7/00
USPC .................................................. 434/236, 238
See application file for complete search history.

(56) References Cited

U.S. PATENT DOCUMENTS

| | | | |
|---|---|---|---|
| 2013/0085808 A1* | 4/2013 | Forbes ................... | G06Q 30/02 705/7.32 |
| 2019/0117142 A1* | 4/2019 | Moskowitz ........... | G06F 40/284 |
| 2019/0172363 A1* | 6/2019 | Arun ...................... | G16H 20/70 |
| 2023/0294293 A1* | 9/2023 | Tosswill .................. | B25J 11/00 345/468 |
| 2023/0410979 A1* | 12/2023 | Reeves ................. | A61B 5/1112 |

* cited by examiner

*Primary Examiner* — Kang Hu
*Assistant Examiner* — Correll T French
(74) *Attorney, Agent, or Firm* — Smart & Biggar LP

(57) ABSTRACT

Methods and devices are described for proactively managing an individual's mental health through the delivery of customized digital wellness content to a user based on their emotional state. In various examples, the present disclosure describes a method at a device. A user input is obtained and mapped to a mood parameter representative of the user's emotional state. Recommended digital wellness content is displayed on a user interface enabling the user to engage with the recommended digital wellness content, based on the mood parameter, and optionally based on the user's historical interaction with digital wellness content. In examples, engaging with the recommended digital wellness content may assist the user in reaching a state of emotional balance and promote wellness.

20 Claims, 23 Drawing Sheets

METHODS AND SYSTEMS FOR INTERACTIVE DELIVERY OF DIGITAL CONTENT RESPONSIVE TO EMOTIONAL STATE

CROSS-REFERENCE TO RELATED APPLICATIONS

This application claims priority to and benefit of U.S. Provisional Patent Application No. 63/408,956 filed Sep. 22, 2022, the contents of which are incorporated by reference.

FIELD

The present disclosure is related to methods and devices for interactive delivery of digital content to a user based on the user's emotional state.

BACKGROUND

The rise of the internet, social media and more recently, working from home has dramatically increased the amount of time that individuals spend looking at, using, and interacting with screens. As a result of increased screen-use, over half of North American workers are impaired, feeling angry and suffering from increased anxiety and stress, a growing health crisis that has been largely ignored and unaddressed. At the same time, individuals have become comfortable with and in some cases prefer digital interactions.

Accordingly, it would be useful to provide a digital solution that can help address the negative effects of anxiety and stress.

SUMMARY

The present disclosure describes systems, methods, and processor-readable media for proactively managing an individual's mental health, and specifically, addressing anxiety and stress through the interactive delivery of customized digital wellness content to users based on their emotional state. In various examples, the present disclosure describes a method at a device. A user input is obtained and mapped to a mood parameter representative of the user's emotional state. Recommended digital wellness content is displayed on a user interface enabling the user to engage and interact with the recommended digital wellness content, based on based on the mood parameter, and optionally based on the user's historical interaction with digital wellness content. In examples, engaging with the recommended digital wellness content may elicit a positive emotional response in the user, thereby assisting the user in reaching a state of emotional balance and promote wellness.

In various examples, the present disclosure also describes methods and devices that enable a server to automatically generate a recommendation of one or more digital wellness content items to serve to a user, based on the emotional state of the user and optionally, the user's interaction history with digital wellness content. Different wellness content items that can be ranked and used to generate a wellness workout routine, based on the emotional state of the user and the user's historical interaction with digital wellness content, and the ranked wellness content items may be provided as a ranked recommendation. The ranked recommendation may enable a user to more easily identify and select a suitable wellness content to interact with to promote positive mental health, for example, to cause a mood enhancing response in the user. In examples, a feedback mechanism (e.g., a machine-learning algorithm or other adaptive algorithm) is implemented by the server, to enable the digital content to be tailored to an individual, not only based on the user's explicit input but also on based on the user's emotional state or other implicit input.

In examples, the delivery of wellness content according to a variety of delivery models, including QR codes, may provide advantages for mood enhancement in users. In various settings, QR codes may offer distinct wellness content tailored to the environment, maximizing emotional intervention efficacy. Particularly in high-stress environments, such as waiting areas, QR codes grant users immediate access to wellness content designed to reduce stress during prolonged waits.

In examples, the incorporation of QR codes may provide advantages in seamlessly delivering targeted wellness interventions to users. In examples, QR codes provide for fast and easy methods for organizations, such as airports, hospitals, educational institutions, sports and entertainment venues, casinos, online gambling or corporate spaces, among others, to deliver on-site, targeted, location-specific wellness content that not only caters to the user's emotional state but also to their physical environment.

In examples, the incorporation of QR codes may provide advantages in delivering timely microbreaks to users in high-stress environments, such as waiting areas or on the phone. Strategic placement of QR codes in areas where individuals typically experience prolonged waiting times, may prove users with immediate access to stress reducing and/or mood enhancing content designed to improve emotional well-being during potentially frustrating periods.

In examples, QR codes may provide advantages in flexibility and scalability for content delivery. In examples, wellness content linked to a QR code can be dynamically updated based on real-time data analysis, without requiring any change to the physical QR code. In various examples, the present disclosure also supports "context-aware" QR codes. Depending on time, day, or in response to global events, the content linked through a QR code can change, for example, to deliver wellness content specifically designed to address collective feelings of anxiety or uncertainty.

In some example aspects, the present disclosure describes a method at a device. The method includes: obtaining a first input indicating a user's emotional state; and displaying, via a user interface for interacting with digital wellness content, one or more recommended wellness content items that are associated with the user's emotional state, the one or more recommended wellness content items being ranked using a recommendation score that is computed based on the first input, with effect that the displayed one or more recommended wellness content items causes a positive emotional response in the user.

In the preceding example aspect of the method, the method may further include: obtaining, via the user interface, a second input indicating the user's emotional state; and displaying, via the user interface, one or more recommended wellness content items that are associated with the user's emotional state, the one or more recommended wellness content items being ranked using a recommendation score that is computed based also on the second input.

In an example aspect of the method, the method may further include: prior to obtaining a first input indicating a user's emotional state: receiving an electronic communication on the electronic device requesting the user provide the first input; and using the electronic communication, obtain the first input indicating the user's emotional state by selecting from a list of available first inputs.

In an example aspect of the method, the method may further include: prior to obtaining a first input indicating a user's emotional state: accessing a public digital wellness content item corresponding to a QR code in proximity to the public digital wellness content item; generating user interaction data corresponding to user interaction activity within a user interface that is associated with the public digital wellness content; and obtaining the first input based on the user interaction data.

In an example aspect of the method, 5. The method of claim 1, wherein obtaining the first input comprises one of: selecting a "good day" input; selecting a "bad day" input; selecting from a list of available first inputs associated with a check-in prompt input; selecting from a list of available first inputs associated with a net promotor score (NPS) input; or selecting from a list of available first inputs associated with a feedback input.

In some example aspects, the present disclosure describes a method at a wellness content server. The method includes: receiving a first input indicating a user's emotional state; mapping a mood parameter to the user's emotional state based on the first input; computing a recommendation score for one or more wellness content items based on the mood parameter; ranking the one or more wellness content items based on the recommendation score to generate one or more recommended wellness content items; and transmitting a signal to cause a display of a remote user device to output the one or more recommended wellness content items, with effect that the displayed one or more recommended wellness content items causes a positive emotional response in the user.

In the preceding example aspect of the method, the method may further include: receiving a second input indicating a user's emotional state; and mapping the mood parameter to the user's emotional state based also on the second input.

In an example aspect of the method, the method may further include: obtaining historical user interaction data for the user describing prior user interaction with one or more digital wellness content items; and mapping the mood parameter based also on the historical user interaction data.

In an example aspect of the method, the method may further include: outputting the user interaction data in a dashboard user interface.

In any of the preceding example aspects of the method, wherein the one or more recommended wellness content items is one or more of: a Droodle™ content item; a puzzle content item; a game content item; a quiz content item; a trivia content item; an artwork content item; a learning content item; a movement content item; an audio content item; a sleep training content item; an autonomous sensory meridian response (ASMR) content item; a microbreak content item; or a podcast content item.

In some example aspects, the present disclosure describes an electronic device. The electronic device includes: a memory storing instructions; and a processing unit coupled to the memory; wherein the processing unit is configured to execute the instructions to cause the device to obtain a first input indicating a user's emotional state; and display, via a user interface for interacting with digital wellness content, one or more recommended wellness content items that are associated with the user's emotional state, the one or more recommended wellness content items being ranked using a recommendation score that is computed based on the first input, with effect that the displayed one or more recommended wellness content items causes a positive emotional response in the user.

In the previous example aspect of the electronic device, wherein the processing unit is configured to execute the instructions to further cause the device to: obtain, via the user interface, a second input indicating the user's emotional state; and display, via the user interface, one or more recommended wellness content items that are associated with the user's emotional state, the one or more recommended wellness content items being ranked using a recommendation score that is computed based also on the second input.

In a previous example aspect of the electronic device, wherein the processing unit is configured to execute the instructions to further cause the device to: prior to obtaining a first input indicating a user's emotional state: receive an electronic communication on the electronic device requesting the user provide the first input; and using the electronic communication, obtain the first input indicating the user's emotional state by selecting from a list of available first inputs.

In a previous example aspect of the electronic device, wherein the processing unit is configured to execute the instructions to further cause the device to: prior to obtaining a first input indicating a user's emotional state: access a public digital wellness content item corresponding to a QR code in proximity to the public digital wellness content item; generate user interaction data corresponding to user interaction activity within a user interface that is associated with the public digital wellness content; and obtain the first input based on the user interaction data.

In some example aspects, the present disclosure describes a non-transitory computer readable medium having instructions encoded thereon, wherein the instructions, when executed by a processing unit of an electronic device, cause the device to: obtain a first input indicating a user's emotional state; and display, via a user interface for interacting with digital wellness content, one or more recommended wellness content items that are associated with the user's emotional state, the one or more recommended wellness content items being ranked using a recommendation score that is computed based on the first input, with effect that the displayed one or more recommended wellness content items causes a positive emotional response in the user.

In some example aspects, the present disclosure describes a content serving system. The content serving system includes: a wellness content server; a memory storing instructions; and a processing unit coupled to the memory; wherein the processing unit is configured to execute the instructions to cause the device to: receive a first input indicating a user's emotional state; map a mood parameter to the user's emotional state based on the first input; compute a recommendation score for one or more wellness content items based on the mood parameter; rank the one or more wellness content items based on the recommendation score to generate one or more recommended wellness content items; and transmit a signal to cause a display of a remote user device to output the one or more recommended wellness content items, with effect that the displayed one or more recommended wellness content items causes a positive emotional response in the user.

In the preceding example aspect of the content serving system, wherein the processing unit is configured to execute the instructions to further cause the system to: receive a second input indicating a user's emotional state; and map the mood parameter to the user's emotional state based also on the second input.

In a preceding example aspect of the content serving system, wherein the processing unit is configured to execute the instructions to further cause the system to: obtain historical user interaction data for the user describing prior user interaction with one or more digital wellness content items; and map the mood parameter based also on the historical user interaction data.

In a preceding example aspect of the content serving system, wherein the processing unit is configured to execute the instructions to further cause the system to: output the user interaction data in a dashboard user interface.

In a preceding example aspect of the content serving system, wherein the one or more recommended wellness content items is one or more of: a Droodle™ content item; a puzzle content item; a game content item; a quiz content item; a trivia content item; an artwork content item; a learning content item; a movement content item; an audio content item; a sleep training content item; an autonomous sensory meridian response (ASMR) content item; a microbreak content item; or a podcast content item.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DETAILED DESCRIPTION

Figure 1:
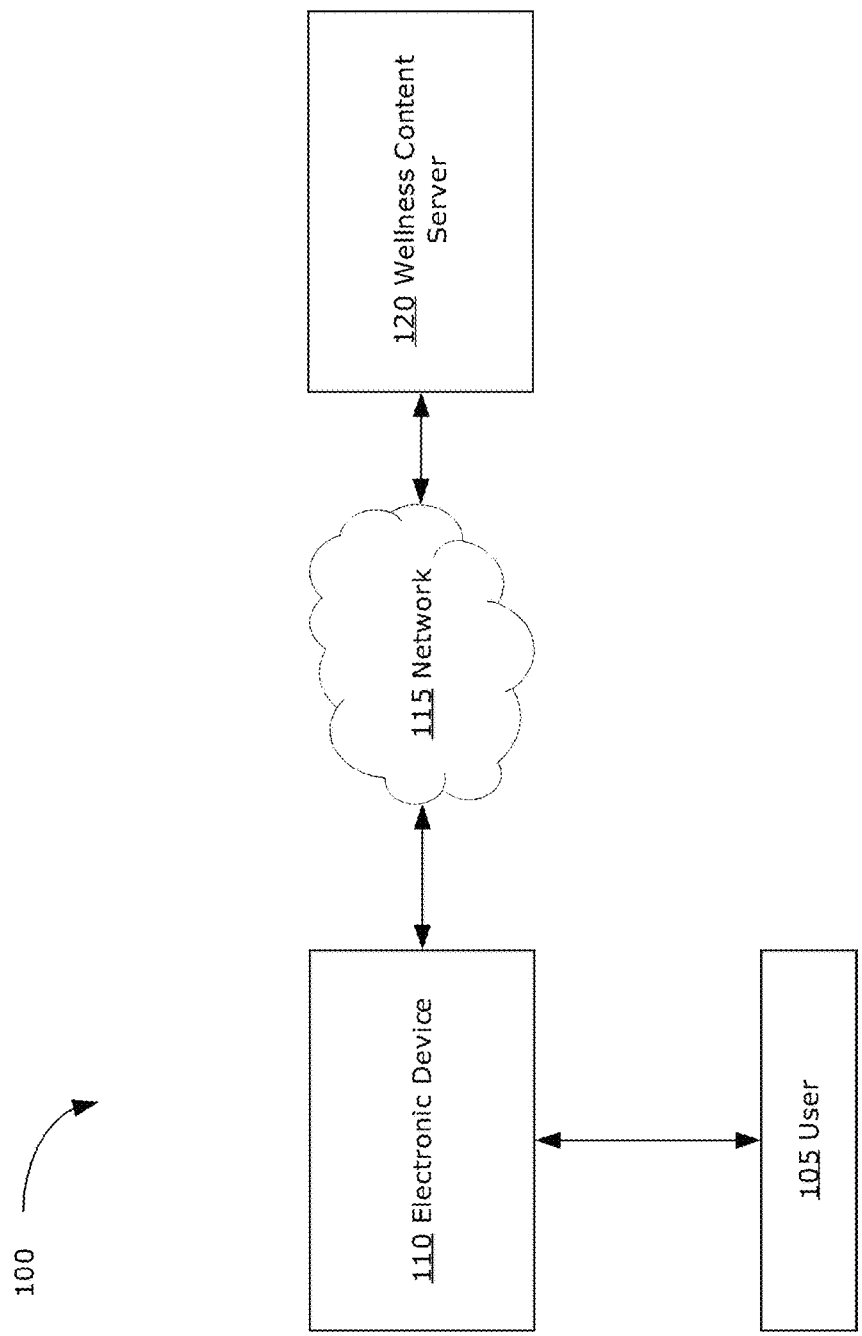
FIG. 1 is a block diagram illustrating an example simplified system in which examples of the present disclosure may be implemented.

The present disclosure describes a mood enhancing technology for proactively managing an individual's mental health, and specifically, addressing anxiety and stress through the delivery of customized digital wellness content to users based on their emotional state. To assist in understanding the present disclosure, the following describes some relevant terminology that may be related to examples disclosed herein.

In the present disclosure, an "emotion" is a strong feeling that a user may experience in the moment in a direct response to a source. Emotions may induce physical responses as well such as body language, facial expressions and sounds.

In the present disclosure, an "emotional state" of a user can mean: A condition experienced by the user that represents how they are feeling in the current moment, for example, stressed, balanced, lacking motivation or burned out, among others. In some examples, the user's emotional state may be indicated by a user's response to a question such as "how are you doing?" or "how is your day going?" or by selecting a position along a cadence scale (e.g. 1-5) among others.

In the present disclosure, "stress level" can mean: a measure of the level of stress an individual is currently experiencing. In examples, stress level may impact a user's emotional state in the short term, and may impact a user's mood over the long term.

In the present disclosure, a "mood" can mean: a less intense state of mind that represents a longer-duration feeling experienced by a user. A mood may not necessarily be triggered by a specific source, but may accumulate in response to many sources over time.

In the present disclosure, a "mood parameter" is a representation, for example, a numeric representation of an emotional state, a mood state or a stress level of a user. For example, a mood parameter may be represented as a value from 1 to 5 on the cadence scale, or a mood parameter may be represented as a value on another numerical scale. In examples, the mood parameter may indicate the level of stress currently experienced by the user. In general, a mood parameter may be detected from implicit user input (e.g., a mood parameter may be implied by the user's engagement with a particular wellness content item or type of wellness content, or may be implied based on prior engagement history with wellness content), or a user may explicitly select a mood parameter (e.g. a mood parameter may be explicitly indicated by a user selecting an option from a set of options provided on a user interface, or by a user controlling a slider on a user interface, etc.).

In the present disclosure, a "fight-or-flight response" can mean: a physiological response triggered by the sympathetic nervous system of an individual, in response to a perceived threat or stress. In examples, the body receives a burst of energy through the release of adrenaline, in preparation for the body to fight or flee from perceived dangers.

In the present disclosure, a "mood enhancing technology" can mean: a technology that causes a positive emotional response in a user or a mood enhancing response in a user.

In the present disclosure, a "mood pattern" can mean: a mapping or an association between an emotional state of a user and a pattern of user interaction with wellness content that is learned over time, based on a history of wellness content interaction by the user. In examples, a mood pattern may be shared by a group of individuals and may be used to serve recommended wellness content to a user when the user exhibits similarities or shares characteristics with the group of individuals, including content viewing patterns, behaviors or moods.

In the present disclosure, a "microbreak" can mean: a short duration mental break in which a user shifts their attention away from the current task and engages in an activity that shifts the user's brain from a stressed or "fight-or-flight" response towards a more balanced, relaxed state. In examples, a microbreak may be a few minutes in duration, ranging for example, from 1 to 5 minutes long, or extending up to 10 minutes.

In the present disclosure, a "warm up" or "digital warm up" can mean: similar to a physical warm up exercise to prepare the body for physical exercise, a digital warm up may be a light, short interaction with a digital wellness content item that improves focus and prepares the user for wellness training.

In the present disclosure, a "good day" can mean: The good day response occurs when the brain no longer perceives danger or the need to run and allows autonomic nervous system functioning to return to normal. Occurrences of a "good day" for a user are recorded and tracked as part of user statistics, and may be explicitly obtained from a user input or may be inferred from user engagement.

In the present disclosure, a "bad day" can mean: a negative feeling associated with high levels of stress and anxiety or a lack of motivation, among other negative feelings. In an example, an individual suffering from high levels of stress and anxiety may attribute their negative feelings to screen stress syndrome, where an individual may feel that they have wasted their time (although they might have been working hard) and achieved nothing and have no time for enjoyment. They may feel cheated, angry, tired and worn out. Occurrences of a "bad day" for a user are recorded and tracked as part of user statistics, and may be explicitly obtained from a user input or may be inferred from user engagement.

In the present disclosure, "digital wellness content", a "digital wellness content item" or a "wellness content item" can mean: certified wellness content that invokes the good day Response™ to mitigate or reduce anger, stress, anxiety and the fight-or-flight response.

In the present disclosure, a "check-in prompt" can mean: a question that asks how the user feels and asks them to rank how they are feeling on a numeric scale, for example, using the cadence scale which allows users to rank their mood on a scale of 1-5. In other examples, a check-in prompt may ask the user to rank how they are feeling based on a list of options, for example, "happy", "content", "bored/stressed", "annoyed" or "stressed", among others. In other examples, a check-in prompt can be a net promotor score (NPS) prompt, for example, a question that asks how likely the user would be to recommend a digital wellness content item to someone else. In examples, a NPS prompt may ask the user to rank how likely they would be to recommend the digital wellness content item on a numerical scale, or based on a list of options, for example, "Yes, I would recommend it", "Maybe, I'm unsure if I would recommend it" or "No, I wouldn't recommend it".

In the present disclosure, "digital real estate" can mean: existing screens currently installed in a public setting, for example, in waiting rooms, airports, bus/subway stations, restaurants and airplanes, among others, which may be repurposed to deliver wellness content to one or more individuals. In examples, "unused digital real estate" can mean: empty wall space where screens could be mounted or existing static artwork that could be replaced with screens and be repurposed to deliver wellness content to one or more individuals.

In the present disclosure, a "Droodle™" can mean: a minimalist visual riddles combining elements of "doodle", "drawing" and "riddle" with a humorous description.

In the present disclosure, "binaural beats" or "binaural sound" can mean: a form of brain entrainment which, according to emerging research, can boost levels of endorphins like serotonin. Binaural occurs when an individual hears two tones simultaneously, each at a different frequency and each in a different ear, the brain creates an additional audible tone. This third tone is called a binaural beat and it is heard by a user at a frequency between the two tones. Beta beats may be used to improve concentration and theta beats may improve creativity and relaxation.

The present disclosure describes examples that may help to address some or all of the above drawbacks of existing technologies.

FIG. 1 is a block diagram illustrating an example simplified system 100 in which examples of the present disclosure may be implemented. The system 100 has been simplified in this example for ease of understanding; generally, there may be more entities and components in the system 100 than that shown in FIG. 1. The system 100 may be a digital wellness system wherein a user 105 may be served digital wellness content on an electronic device 110 and may include a network 115. The network 115 may be any form of network (e.g., an intranet, the Internet, a P2P network, a WAN and/or a LAN). The system 100 includes a server (e.g. wellness content server 120), which communicates with the electronic device 110 to send or receive data, services or applications for the purposes of managing mental health or wellness, or for associated data processing and storage. The term "server", as used herein, is not intended to be limited to a single hardware device: the server 120 may include a server device, a distributed computing system, a virtual machine running on an infrastructure of a datacenter, or infrastructure (e.g., virtual machines) provided as a service by a cloud service provider, among other possibilities. Generally, the server 120 may be implemented using any suitable combination of hardware and software, and may be embodied as a single physical apparatus (e.g., a server device) or as a plurality of physical apparatuses (e.g., multiple machines sharing pooled resources such as in the case of a cloud service provider).

Figure 2A:
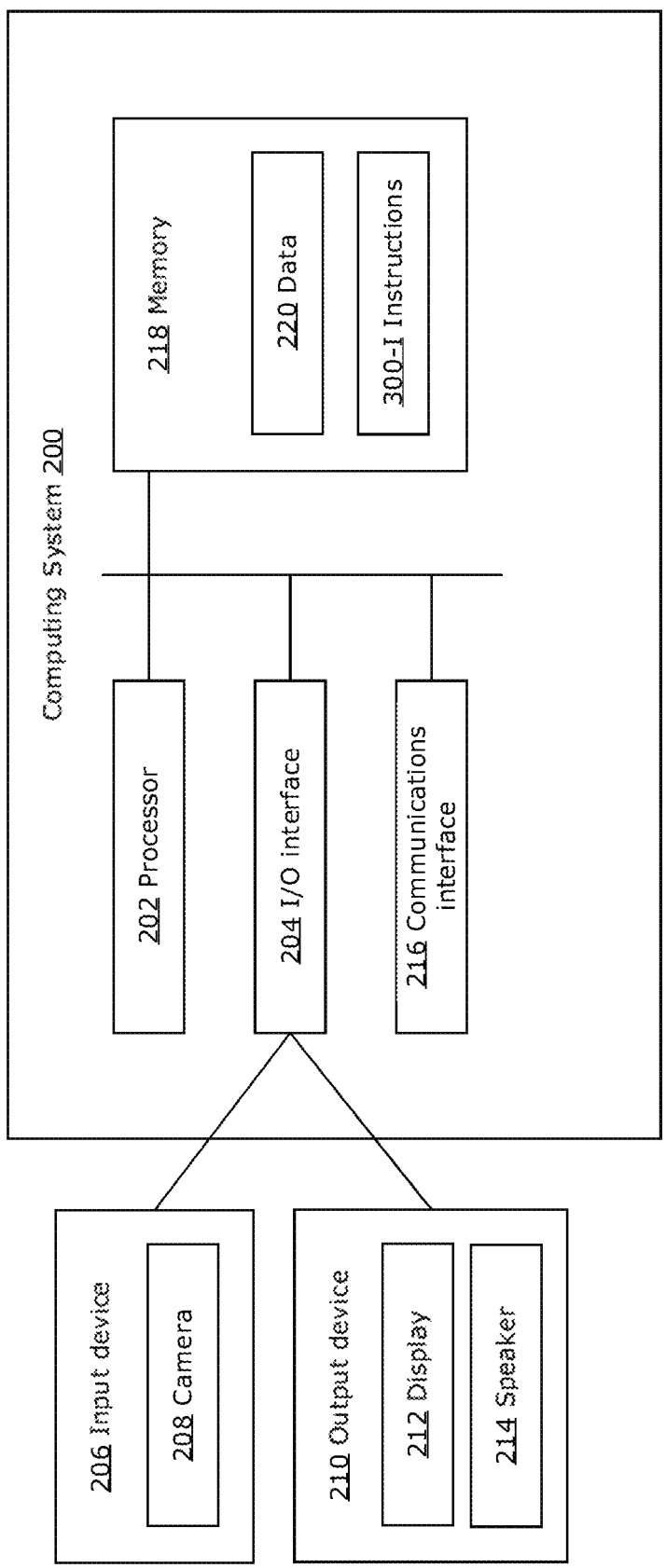
FIG. 2A is a block diagram illustrating an example hardware structure of a computing system that is suitable for implementing embodiments of the present disclosure.

FIG. 2A is a block diagram illustrating an example hardware structure of a computing system 200 that is suitable for implementing embodiments described herein. Examples of the present disclosure may be implemented in other computing systems, which may include components different from those discussed below. The computing system 200 may be used to execute instructions for serving recommended digital wellness content to a user 105, using any of the examples described herein. The computing system 200 may also be used to train blocks of the digital content delivery system 300, or blocks of the digital content delivery system 300 may be trained by another computing system.

Although FIG. 2A shows a single instance of each component, there may be multiple instances of each component in the computing system 200. Further, although the computing system 200 is illustrated as a single block, the computing system 200 may be a single physical machine or device (e.g., implemented as a single computing device, such as a single workstation, single end user device, single server, etc.), and may include mobile communications devices (e.g. smartphones), laptop computers, tablets, desktop computers, smart appliances, wearable devices, assistive technology devices, virtual reality devices, augmented reality devices, Internet of Things (IoT) devices, interactive kiosks, advertising and interactive signage, and educational tools, among others The computing system 200 includes at least one processor 202, such as a central processing unit, a microprocessor, a digital signal processor, an application-specific integrated circuit (ASIC), a field-programmable gate array (FPGA), a dedicated logic circuitry, a dedicated artificial intelligence processor unit, a graphics processing unit (GPU), a tensor processing unit (TPU), a neural processing unit (NPU), a hardware accelerator, or combinations thereof The computing system 200 may include an input/output (I/O) interface 204, which may enable interfacing with an input device 206 and/or an output device 210. In the example shown, the input device 206 (e.g., a keyboard, a mouse, a microphone, a touchscreen, and/or a keypad) may also include a camera 208, for example, to capture or scan a QR code 810 for navigating to an associated digital wellness content item or another webpage. In the example shown, the output device 210 (e.g., a display 212, a speaker 214 and/or a printer) are shown external to the computing system 200. In other example embodiments, there may not be any input device 206 and output device 210, in which case the I/O interface 204 may not be needed.

The computing system 200 may include at least one communications interface 216 for wired or wireless communication with other computing systems (e.g., other computing systems in a network). The communications interface 216 may include wired links (e.g., Ethernet cable) and/or wireless links (e.g., one or more antennas) for intra-network and/or inter-network communications.

The computing system 200 may include one or more memories 218 (collectively referred to as "memory 218"), which may include a volatile or non-volatile memory (e.g., a flash memory, a random access memory (RAM), and/or a read-only memory (ROM)). The non-transitory memory 218 may store instructions for execution by the processor 202, such as to carry out examples described in the present disclosure. For example, the memory 218 may store instructions for implementing any of the methods disclosed herein. The memory 218 may include other software instructions, such as for implementing an operating system (OS) and other applications/functions. The instructions can include instructions 300-I for implementing and operating the digital content delivery system 300 described below with reference to FIG. 3. The memory 218 may also include other data 220, information, rules, policies, and machine-executable instructions described herein.

In some examples, the computing system 200 may also include one or more electronic storage units (not shown), such as a solid state drive, a hard disk drive, a magnetic disk drive and/or an optical disk drive. In some examples, data and/or instructions may be provided by an external memory (e.g., an external drive in wired or wireless communication with the computing system 200) or may be provided by a transitory or non-transitory computer-readable medium. Examples of non-transitory computer readable media include a RAM, a ROM, an erasable programmable ROM (EPROM), an electrically erasable programmable ROM (EEPROM), a flash memory, a CD-ROM, or other portable memory storage. The storage units and/or external memory may be used in conjunction with memory 218 to implement data storage, retrieval, and caching functions of the computing system 200. The components of the computing system 200 may communicate with each other via a bus, for example.

Figure 2B:
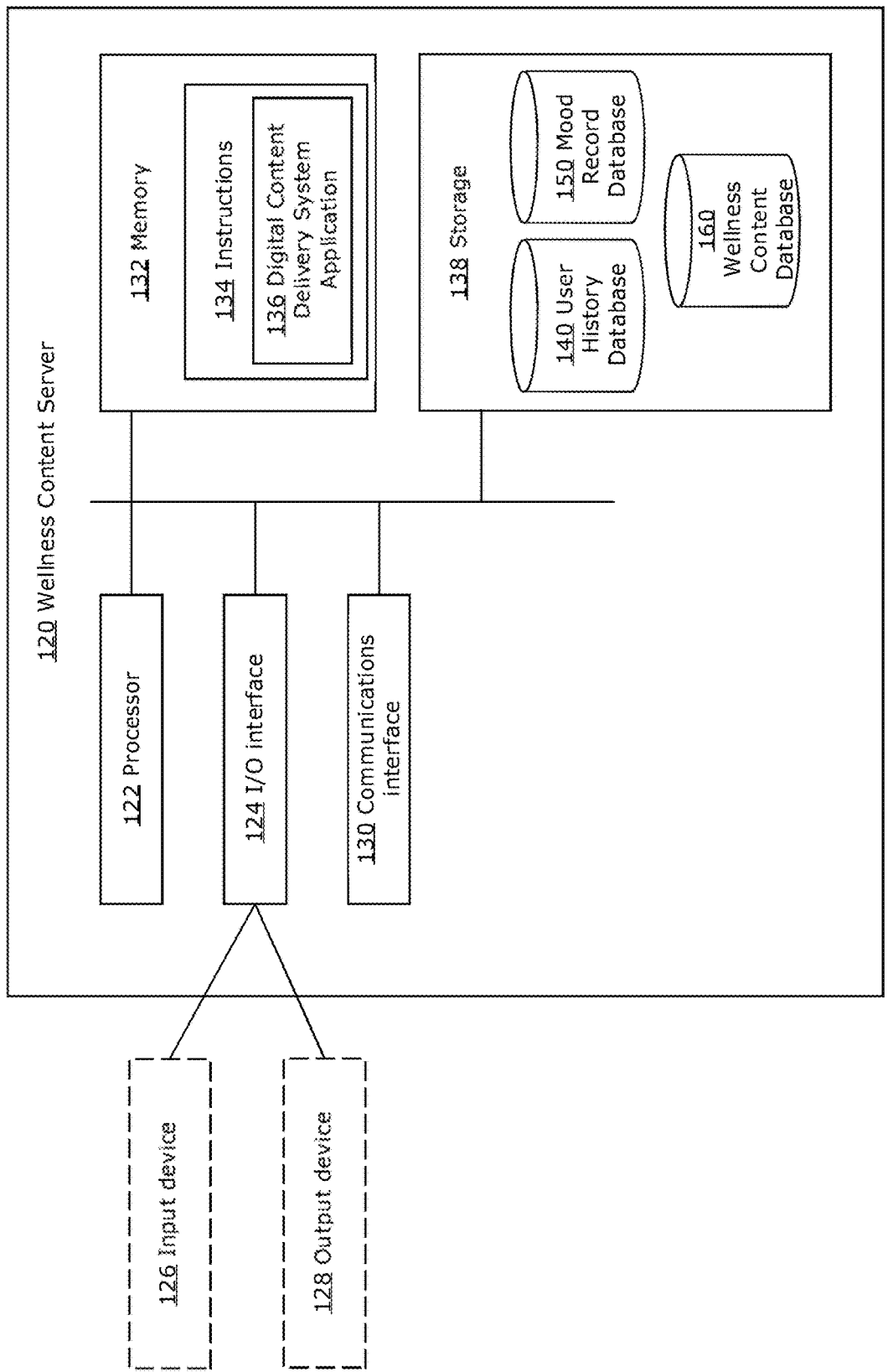
FIG. 2B is a block diagram of an example server that may be used to implement examples described herein.

FIG. 2B is a block diagram illustrating an example implementation of the wellness content server 120 that is suitable for implementing embodiments described herein. Examples of the present disclosure may be implemented in other computing systems, which may include components different from those discussed below. The wellness content server 120 may be used to execute instructions for serving recommended digital wellness content to a user 105, using any of the examples described herein. The wellness content server 120 may also be used to train blocks of the digital content delivery system 300, or blocks of the digital content delivery system 300 may be trained by another computing system.

The wellness content server 120 includes one or more processors 122, such as a CPU, a microprocessor, a digital signal processor, an application-specific integrated circuit (ASIC), a field-programmable gate array (FPGA), a dedicated logic circuitry, a dedicated artificial intelligence processor unit, or combinations thereof. The wellness content server 120 may also include one or more optional input/output (I/O) interfaces 124, which may enable interfacing with one or more optional input devices 126 and/or optional output devices 128.

In the example shown, the input device(s) 126 (e.g., a keyboard, a mouse, a microphone, a touchscreen, and/or a keypad) and output device(s) 128 (e.g., a display, a speaker and/or a printer) are shown as optional and external to the wellness content server 120. In other examples, there may not be any input device(s) 126 and output device(s) 128, in which case the I/O interface(s) 124 may not be needed.

The wellness content server 120 may include one or more communications interfaces 130 for wired or wireless communication with the network 115, or another entity or node in the system 100. The communications interface(s) 124 may include wired links (e.g., Ethernet cable) and/or wireless links (e.g., one or more antennas) for intra-network and/or inter-network communications.

The wellness content server 120 may also include one or more storage units 138, which may include a mass storage unit such as a solid state drive, a hard disk drive, a magnetic disk drive and/or an optical disk drive. The storage unit(s) 138 may store a plurality of data within one or more local databases, for example, a user history database 140, a mood record database 150 and a wellness content database 160 as discussed further below.

The wellness content server 120 may include one or more memories 132, which may include a volatile or non-volatile memory (e.g., a flash memory, a random access memory (RAM), and/or a read-only memory (ROM)). The non-transitory memory(ies) 132 may store instructions for execution by the processor(s) 122, such as to carry out examples described in the present disclosure. The memory(ies) 132 may include other software instructions, such as for implementing an operating system and other applications/functions. In some examples, the memory(ies) 132 may include software instructions 134 for execution by the processor 122 to run one or more applications, for example, a digital content delivery system application 136. In examples, the digital content delivery system application 136 may include a user interface, for example, to facilitate a user 105 interacting with and/or navigating a digital wellness platform on their electronic device 110. In some examples, the wellness content server 120 may additionally or alternatively execute instructions from an external memory (e.g., an external drive in wired or wireless communication with the wellness content server 120) or may be provided executable instructions by a transitory or non-transitory computer-readable medium. Examples of non-transitory computer readable media include a RAM, a ROM, an erasable programmable ROM (EPROM), an electrically erasable programmable ROM (EEPROM), a flash memory, a CD-ROM, or other portable memory storage.

Figure 3:
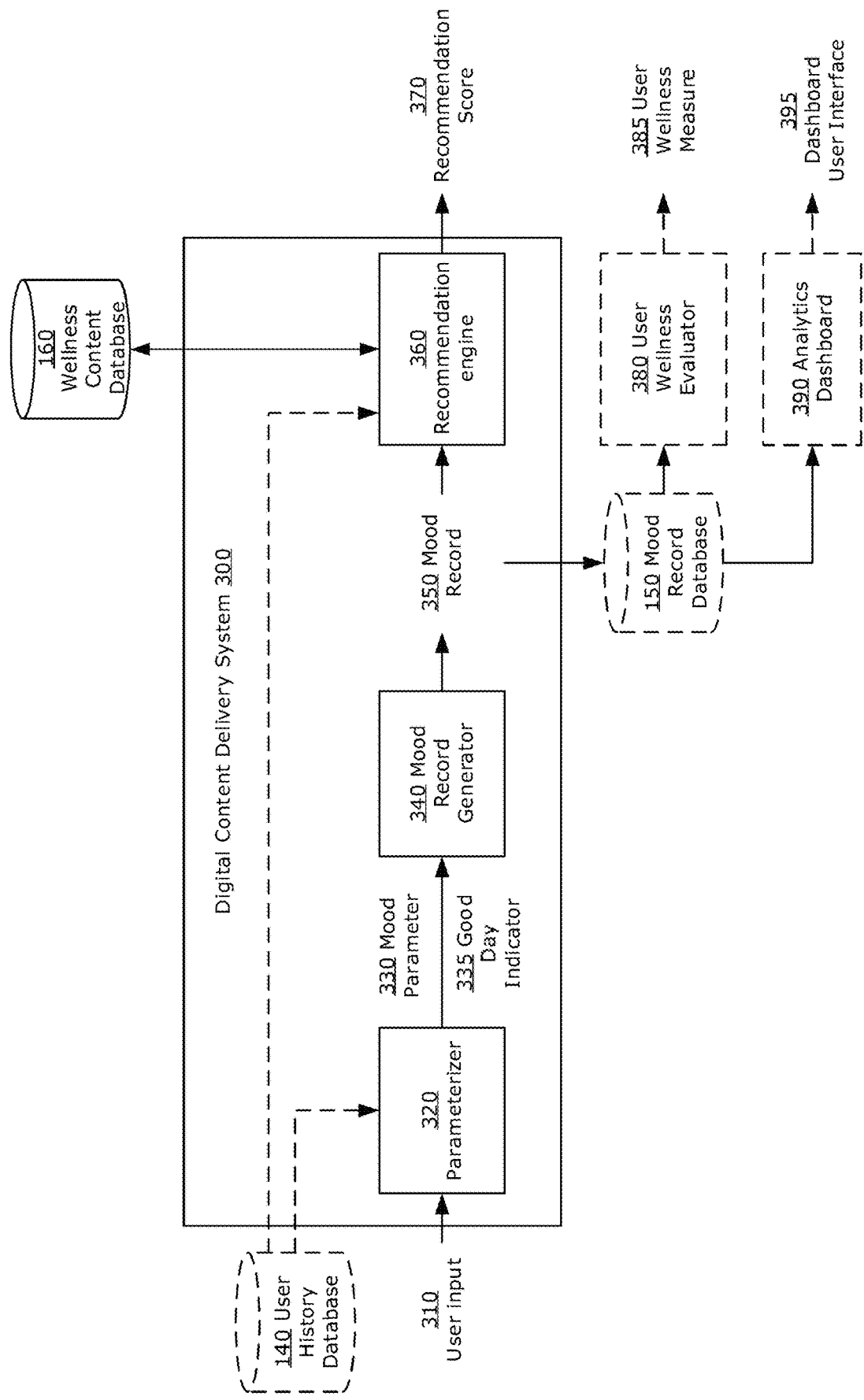
FIG. 3 is a is a block diagram illustrating an example architecture of the digital content delivery system, in accordance with examples of the present disclosure.

FIG. 3 is a is a block diagram illustrating an example architecture of the digital content delivery system 300 that may be used to implement methods to serve digital wellness content to a user 105, in accordance with examples of the present disclosure.

In some examples, the digital content delivery system 300 receives a user input 310 representing the user's emotional state and outputs a recommendation score 370 associated with digital wellness content items to facilitate serving recommended digital wellness content to the user 105. The user input 310 may be obtained explicitly, for example, when the user selects or enters an input on an electronic device 110 representing their emotional state, or the user input 310 may be obtained implicitly, for example, inferred from historical user interaction with digital wellness content on an electronic device 110 or inferred from another source, for example, a net promotor score prompt.

Explicit and implicit user input 310 describing the emotional state of the user 105 may be obtained from various sources, depending on the delivery model. Example delivery models and user inputs 310 are described below. For example, if the delivery model is via email or another form of electronic communication, the user may be prompted in the email with a first question (e.g. how are you doing?) and provided with a discrete number of potential responses. In examples, the user 105 may select a response, for example a positive response (e.g. "good day") or negative response (e.g. "bad day"). In examples, the user 105 may be directed to a specific page on the digital wellness platform (e.g. via a user interface) depending on the response to the first question.

In examples, a parameterizer 320 may receive the user input 310 and may interpret or classify the user input 310 to output a mood parameter 330 as a numerical representation of the user's emotional state. In examples, the parameterizer 320 may map the responses to the first question (e.g. "good day" or "bad day") to a numeric value to generate the mood parameter 330, or the parameterizer 320 may require further information from the user to generate the mood parameter 330. In examples, a second question may be posed to the user 105 in the form of a "check-in prompt", for example the user 105 may be asked to rate their mood on a numeric scale, for example, on a cadence scale 400 and may select a response, for example, on a scale of 1-5. In examples, the parameterizer 320 may interpret or classify the user's response to the second question and generate the mood parameter 330, or the parameterizer 320 may generate the mood parameter 330 based on other information.

In other examples, if the delivery model is based on user interaction with a public digital wellness content item, for example, corresponding to a QR code in proximity to the public digital wellness content item or a QR code in a predetermined location, the user may be served one or more "check-in prompts" while engaging with digital wellness content to generate the user input 310. In examples, the parameterizer 320 may map the responses to the one or more "check-in prompts" to a numeric value to generate the mood parameter 330, or the parameterizer 320 may require further information from the user to generate the mood parameter 330.

Figure 4:
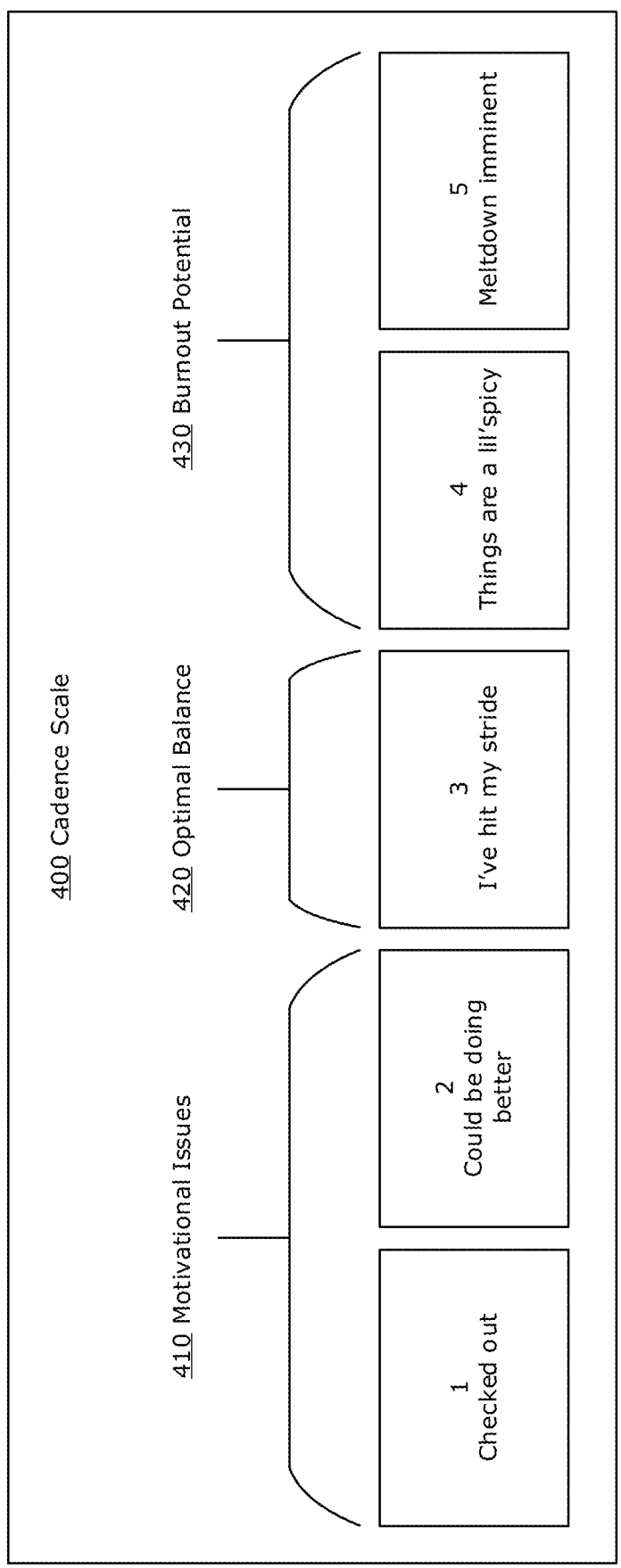
FIG. 4 is an example of a Cadence scale, in accordance with examples of the present disclosure.

FIG. 4 is an example of a Cadence scale 400, in accordance with examples of the present disclosure. In examples, the cadence scale 400 may be a numerical scale from 1-5, where each value on the scale is associated with a level of stress currently being experienced by a user 105, for example, with values at the extremes of the scale (e.g. 1 and 5) indicating high levels of stress and values in the middle of the scale (e.g. 3) indicating a balanced stress level. In examples, a value of 1 or 2 on the cadence scale may indicate that the user has motivational issues 410, including a lack of motivation, for example, with a value of 1 associated with feeling "checked out" or a value of 2 associated with the user feeling that they "could be doing better". In examples, a value of 3 on the cadence scale may indicate that the user is feeling good and has reached an optimal balance 420 with respect to stress, for example "I've hit my stride". In examples, a value of 4 or 5 on the cadence scale may indicate that the user is experiencing burnout potential 430 or is in a "fight or flight" neurological response, for example, with a value of 4 associated with "things are a lil'spicy" or a value of 5 associated with "meltdown imminent".

Returning to FIG. 3, in some embodiments, for example, the parameterizer 320 maps a numeric value to the user input to describe the user's emotional state, mood or stress level, to generate the mood parameter 330. In examples, the parameterizer 320 may rely on predefined rules stored in memory to map between user input 310 and the mood parameter 330 (e.g. a "good day"=3 or a "bad day"=5, or mapping the mood parameter based on a selection on the cadence scale or a selection on another scale, in response to a check-in prompt).

In other embodiments, for example, the parameterizer 320 may dynamically assign a mood parameter 330 for the user 105 based on the user's historical interaction with digital wellness content and/or user preferences. In examples, the parameterizer 320 may be a machine learning model, a rules-based classifier or another model and the user input 310 may be a learned feature based on the user's historical interaction with digital wellness content. For example, if a user 105 has a history of navigating to a certain wellness content item or wellness content type when they are highly stressed (e.g. watching a favorite video), the parameterizer 320 may learn to recognize the emotional state of the user based on the wellness content being accessed. In another embodiment, the parameterizer 320 may classify the user 105 based on their historical interaction with wellness content and based on the historical interaction with wellness content of other users who may or may not share certain characteristics including content viewing patterns, behaviors or moods with the user 105. For example, the user 105 may be classified as having a degree of similarity to a group of other users based on engagement history with digital wellness content or other data, for example, the user's location, the time of day at which the content was accessed, etc. In examples, the user 105 may not be classified as being similar to a group of other users based on shared or similar demographics.

Optionally, the parameterizer 320 may additionally or alternatively output a good day indicator 335, for example, capturing the user's positive "good day" response or negative "bad day" in a binary format (e.g. "good day"=1, "bad day"=0) or another computer-readable format.

In examples, a mood record generator 340 receives the mood parameter 330 and optionally the good day indicator 335 and generates a mood record 350. In examples, the mood record may be stored in the mood record database 150.

Figure 5:
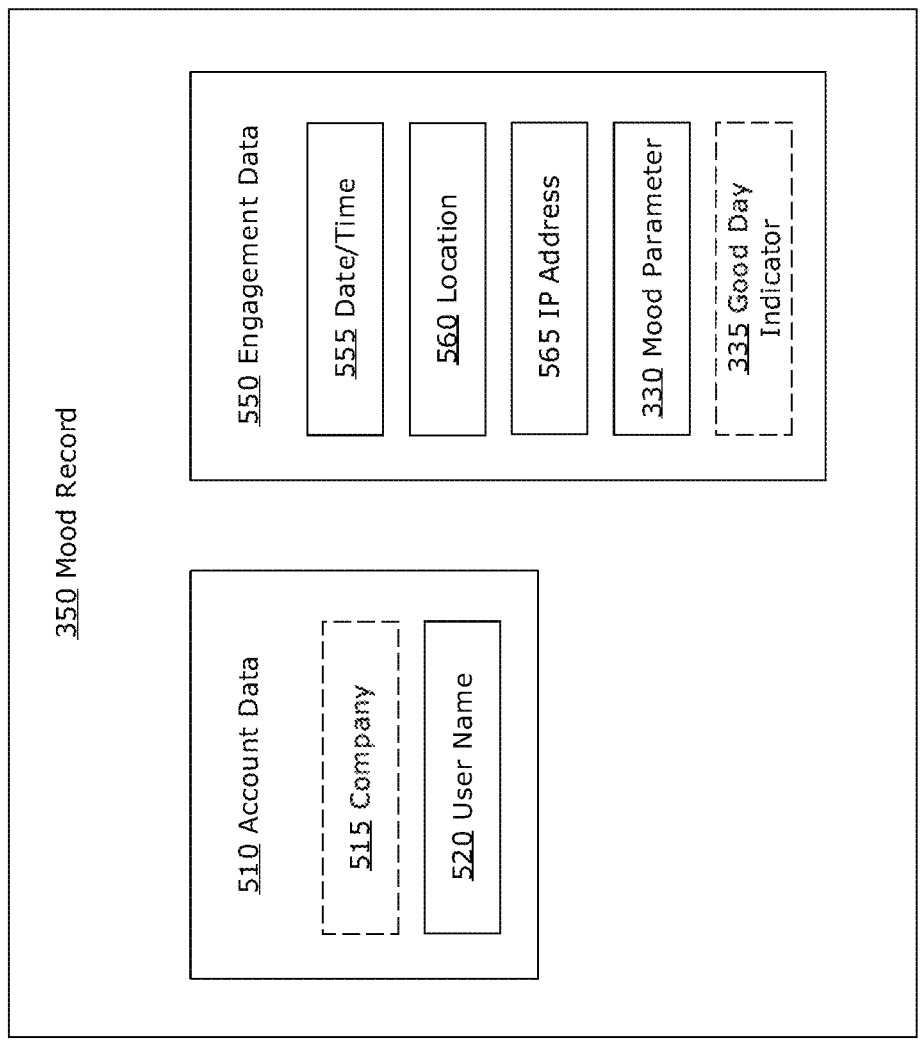
FIG. 5 is an example of a mood record, in accordance with examples of the present disclosure.

FIG. 5 shows an example of a mood record 350, in accordance with examples of the present disclosure. In examples, a mood record 350 may be an entry in a database, for example, a mood record database 150, where the mood record 350 captures data relevant to the user and for a specific interaction instance on the digital wellness delivery system 300. In examples, the mood record 350 may capture account data 510 relevant to the user account of the user 105. In some embodiments, the company 515 associated with the user account may be recorded (e.g. if the user's company has a subscription to the digital wellness delivery system). In examples, a user name 520 may also be recorded. In some embodiments when a user does not have an user account or is not logged in to their user account, an entry of "anonymous" may be recorded for the user name 520. In examples, engagement data 550 relevant to the user's engagement with digital wellness content during a specific interaction instance on the digital wellness delivery system 300 may also be recorded. In examples, the date and/or time 555 of the engagement may be recorded along with the location 560 of the user. In examples, location may be a geolocation of a user (e.g. GPS coordinates associated with a user's electronic device 110 or a location inferred based on a user interaction with a distinct QR code having a predetermined location) or the location may be classified based on the geolocation of the user, for example, "airport", "baggage", "security", "customs", "office", "waiting room", "casino", "arena", "stadium", "concessions" etc. In examples, the user's IP address 565 may also be recorded in the mood record 350 along with the mood parameter 330 and optionally, the good day indicator 335. It should be understood that collection of such data may be subject to the user's consent. In examples where user consent to collect such data is not obtained, such data may not be collected, may be collected in an anonymized manner, or only non-specific and non-identifying data may be collected.

Returning to FIG. 3, the recommendation engine 360 may receive the mood record 350 and may generate a recommendation score 370 associated with one or more digital wellness content items, to facilitate serving recommended digital wellness content to the user 105. In examples, the recommended digital wellness content may be delivered to the user 105 by a user interface on the user's electronic device 110.

In examples, the recommendation engine 360 interfaces with the wellness content database 160 to evaluate and rank the digital wellness content items that best match the user's current emotional state. Digital wellness content may take many forms. Each wellness content item is designed to introduce a short "microbreak" in the user's day while invoking the "good day response" in the user. For example, if a user is experiencing a stressed emotional state, the wellness content may help to shift the user's mood toward a less stressed or more balanced state. Types of digital wellness content may include: a Droodle™; a puzzle or game; artwork, generally by BIPOC artists and including an artist biography; a learning exercise; a movement exercise; an audio element including music or "binaural beats" where the tempo and frequencies of the sound are mapped to a mood parameter or cadence scale, for example, binaural content mapped to the high end of the scale (e.g. approaching burnout) may be slower and feature binaural beats that induce a meditative Theta state whereas binaural content mapped to the low end may feature binaural beats that promote a Beta state for motivation; sleep tips/training exercises; Autonomous Sensory Meridian Response (ASMR) where ASMR represents a tingling sensation on the scalp and along the back of the neck and upper spine that users may find relaxing and podcast, among others.

In examples, recommended wellness content served to a user in the user interface may be a single digital wellness content item that has been ranked by the recommendation score 370 or the recommended wellness content may be more than one content item organized and displayed in the user interface in a sequence representing a digital wellness workout routine 600, depending on the emotional state of the user (which may be explicitly indicated by the user or implicitly inferred by the digital content delivery system 300, as discussed previously). In examples, the workout routine may include wellness content items classified by function, for example, as a warm-up, a training exercise and a recovery exercise or any combination, or the workout routine 600 may include other types of exercises depending on the emotional state of the user. In examples, the recommended workout routine 600 may be different depending on the emotional state of the user. For example, if a user is unmotivated or experiencing feelings of stress, the recommended workout routine 600 may help to guide the user on a path to a state of balance. In other examples, if a user is successfully in a state of balance, the workout routine 600 may represent a training routine, to help strengthen the user's ability to stay in a state of balance. In this way, the digital content delivery system 300 may seamlessly guide the user through a series of digital wellness exercises that are responsive to their current emotional state.

Figure 6:
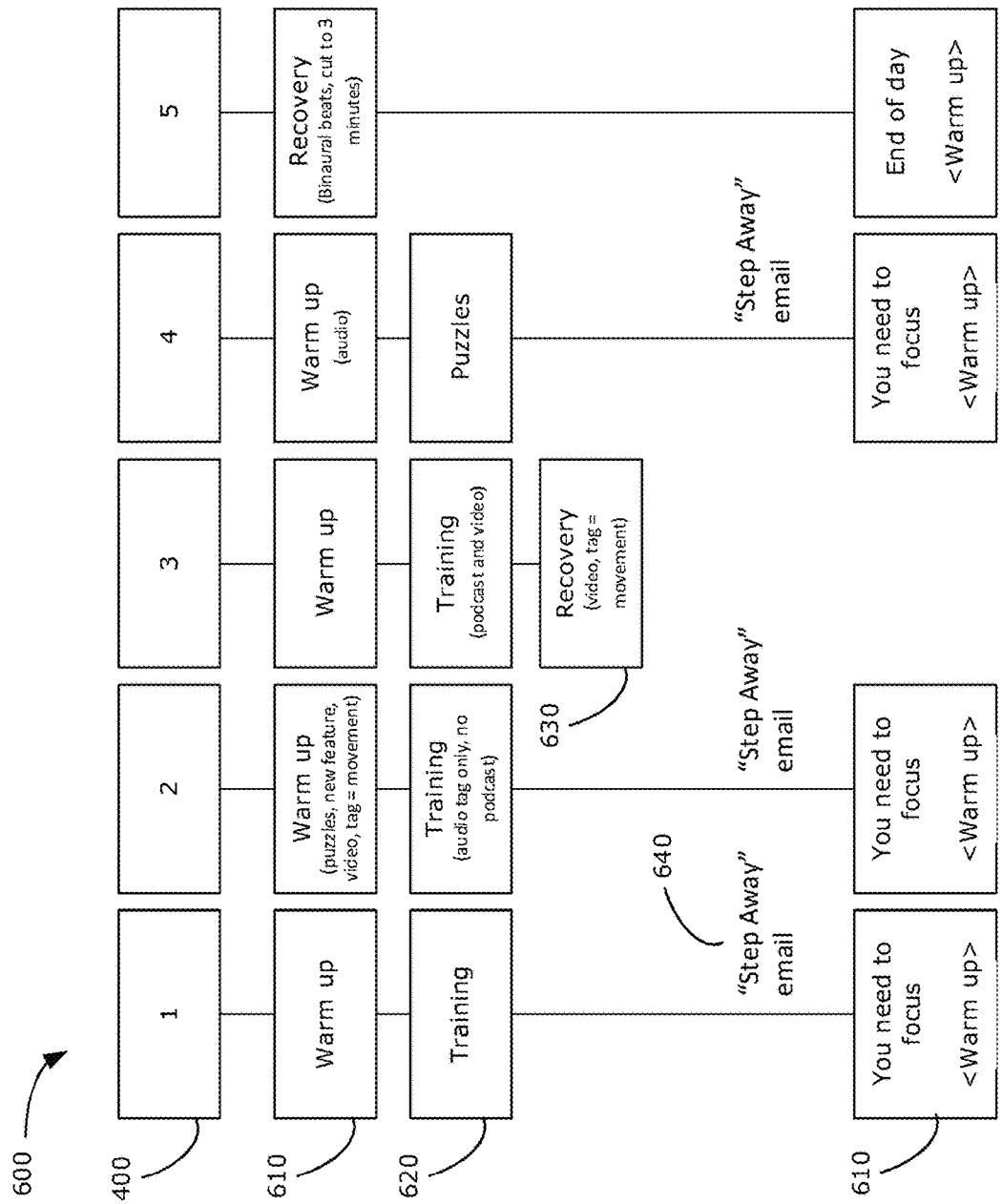
FIG. 6 is an example approach for assembling digital wellness content items into a wellness workout routine, in accordance with examples of the present disclosure.

FIG. 6 is an example approach for assembling digital wellness content items into a wellness workout routine 600, in accordance with examples of the present disclosure. In an embodiment, for example, the recommendation score 370 may be used to serve the highest ranked "warm up" content item 610 and the highest ranked "training" content item 620 and the highest ranked "recovery" content item 630 for a user who identifies as having a balanced emotional state (e.g. cadence value of 3). In another embodiment, for example, the recommendation score 370 may be used to serve the highest ranked "recovery" content item 630 for a user who identifies as being in a highly stressed emotional state (e.g. cadence value of 5). In examples, other combinations of content types may be used to deliver the optimal therapeutic benefit to the user based on their emotional state, interaction history and preferences. In other examples, a user may be served a "step away" email 640 as part of the wellness workout routine 600 causing the user to be served with a highest ranked "warm up" content item 610 to assist with regaining focus or at the end of the day, among others.

In some embodiments, for example, the digital content delivery system 300 may incorporate gamification features to encourage user interaction and engagement, and to motivate users to return to the digital content delivery system 300. Examples may include collecting points upon engaging with a wellness content item, earning badges for accumulating points or completing challenges, among others. Users may then spend their accumulated points on various rewards.

Returning to FIG. 3, optionally, the mood record 350 may be stored in a mood record database 150. In examples, a user wellness evaluator 380 may analyze mood record data, for example, information associated with the mood parameter 330 or good day indicator 335. In examples, assessing the number of "good days" reported by the user compared to the number of "bad days" using the good day indicator 335, the user wellness evaluator 380 may identify trends or statistical relationships related to the emotional state of the user over time. In example, the user wellness evaluator 380 may output one or more user wellness measures 385 to quantify any changes in the user's emotional state over time.

Figure 8A:
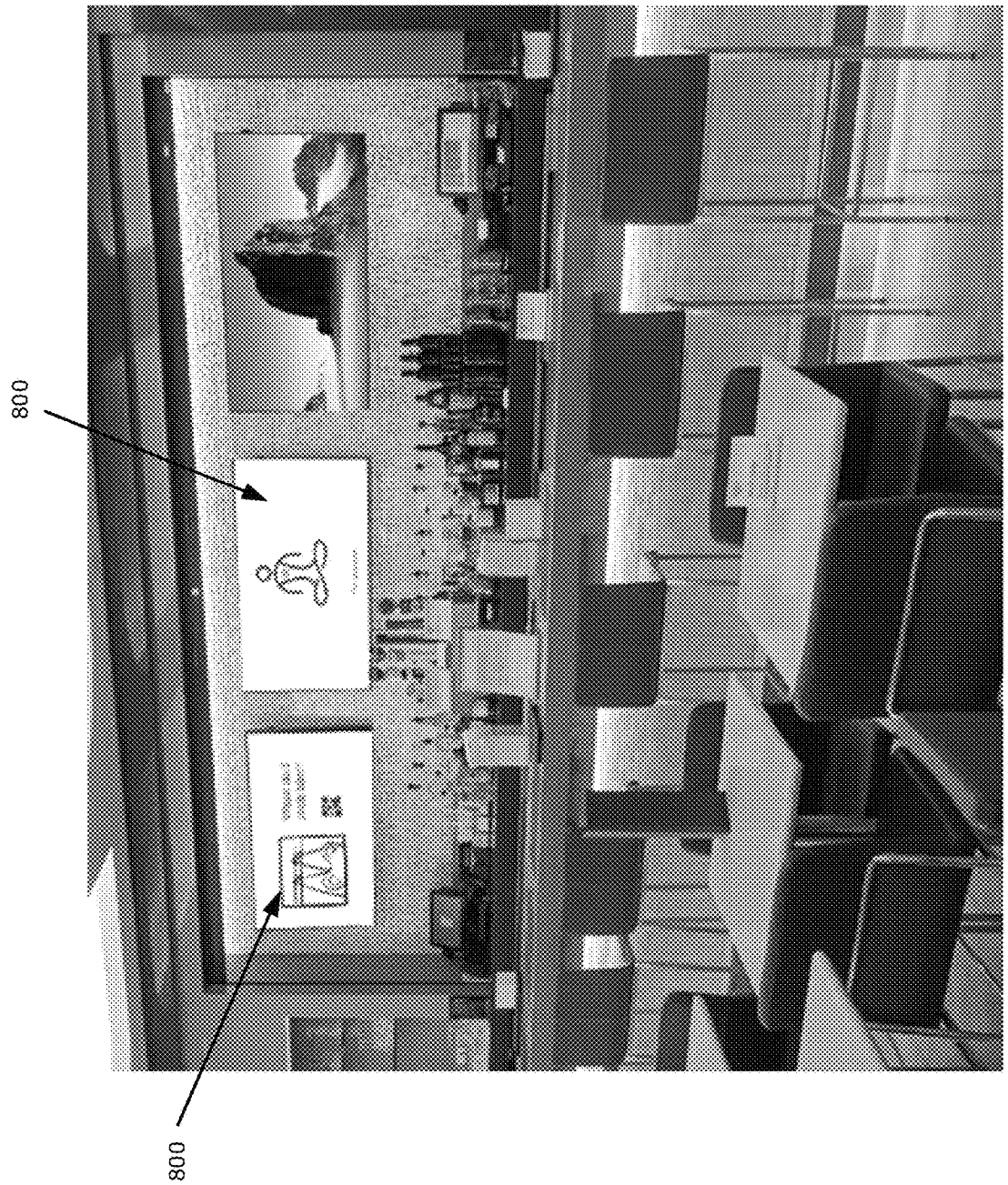
FIG. 8A is an example of wellness content on one or more wall-mounted screens in a bar or restaurant, in accordance with an embodiment of the present disclosure.
Figure 8B:
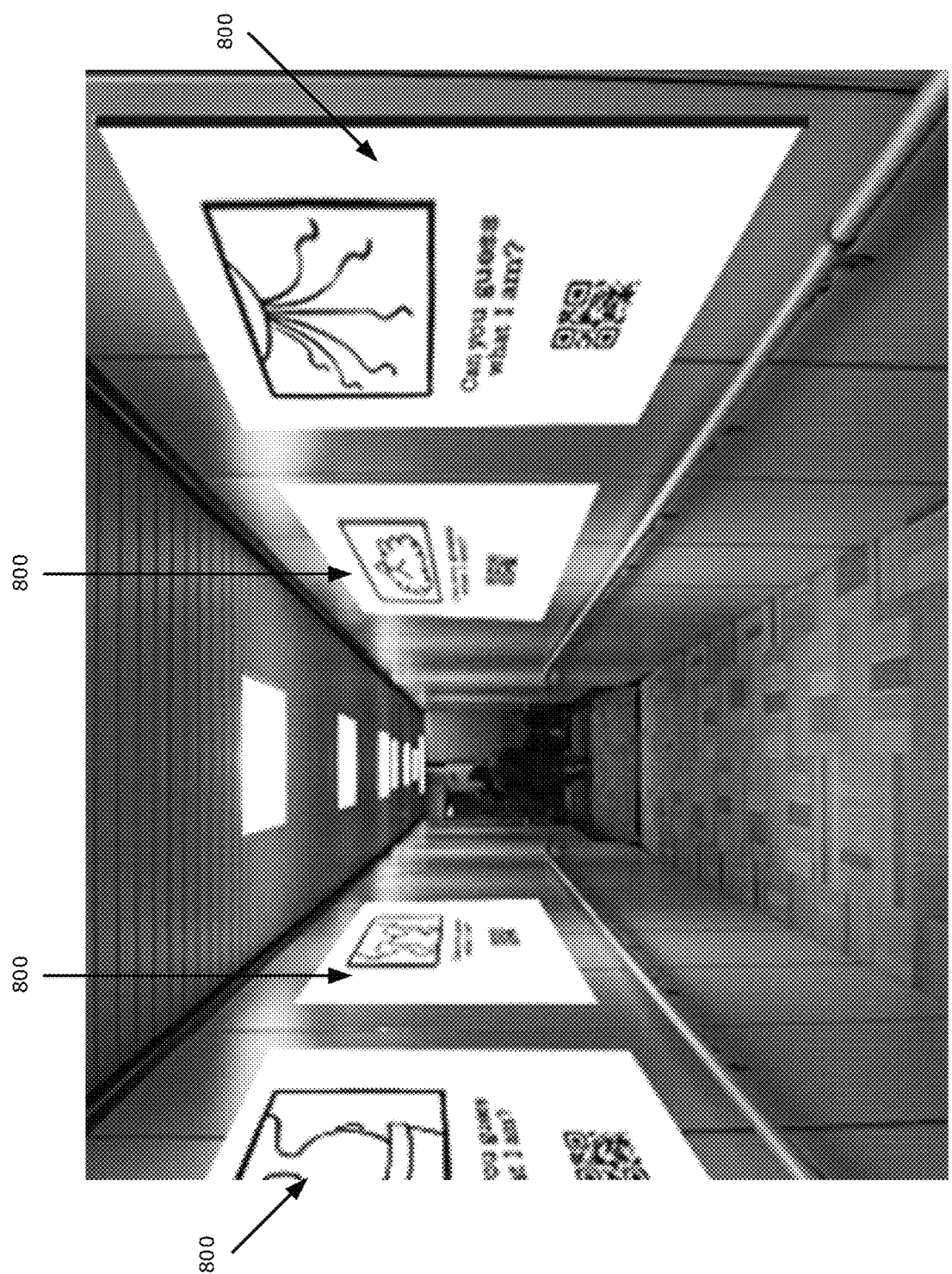
FIG. 8B is an example of wellness content on one or more wall-mounted screens in an airport walkway or passenger boarding bridge, in accordance with an embodiment of the present disclosure.
Figure 8C:
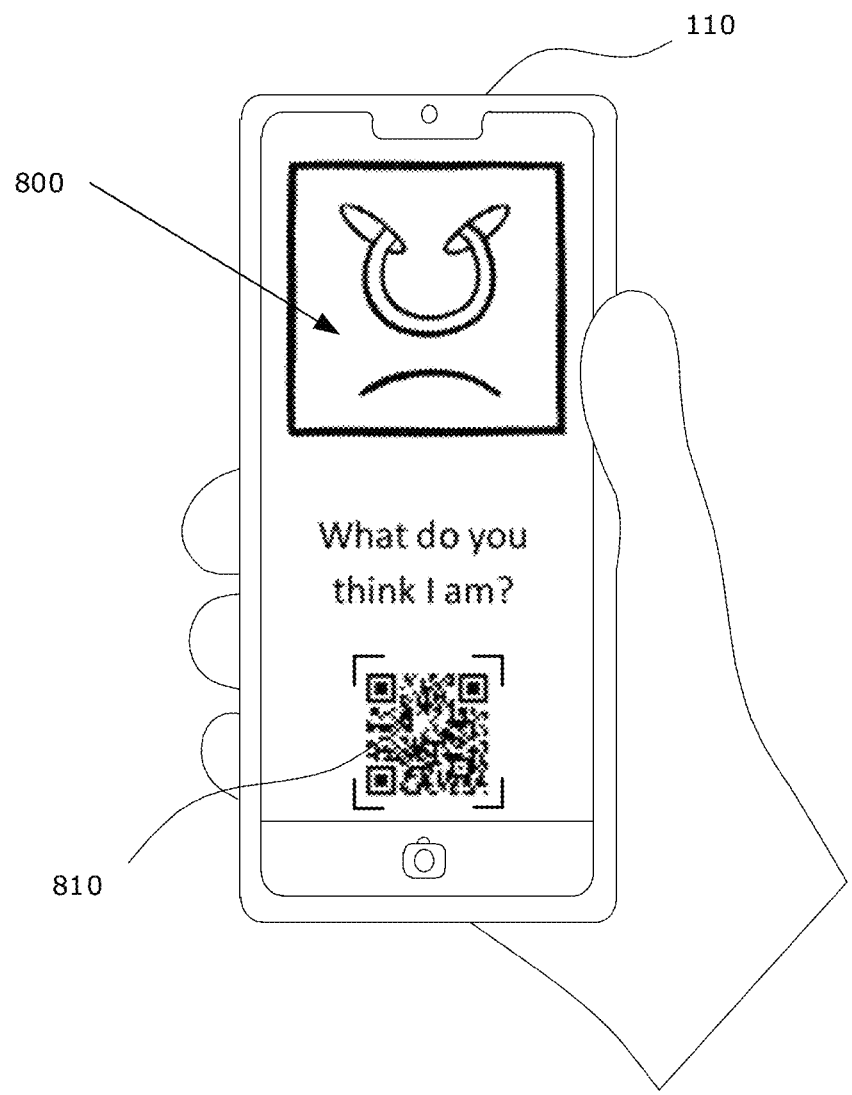
FIG. 8C is an example of a wellness content with an associated QR code being scanned by a camera application on an electronic device, in accordance with an example embodiment of the present disclosure.
Figure 8D:
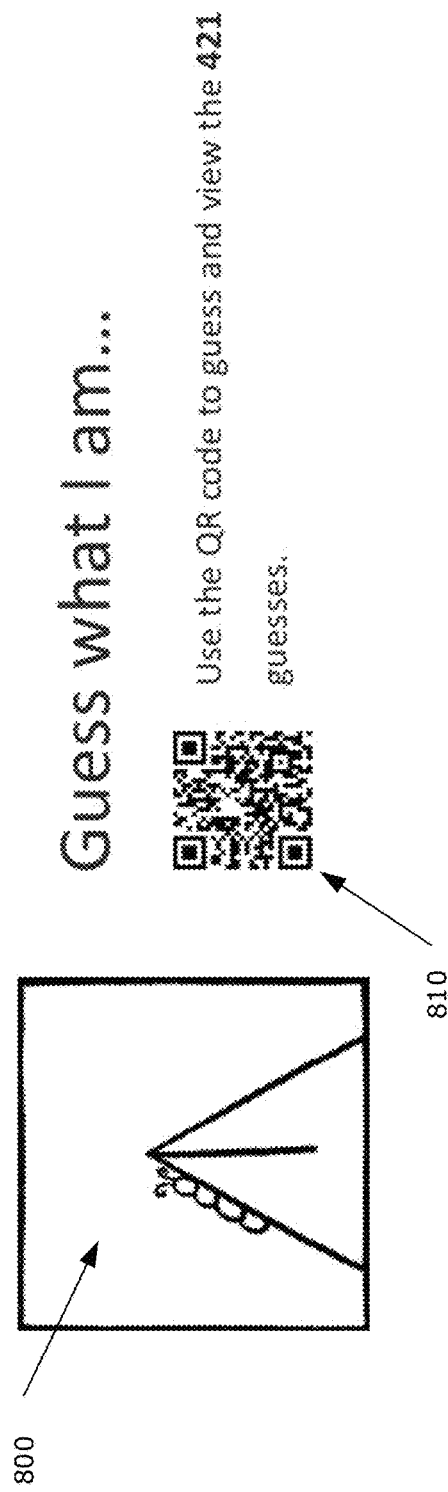
FIG. 8D is an example of a wellness content with an associated QR code, in accordance with examples of the present disclosure.
Figure 8E:
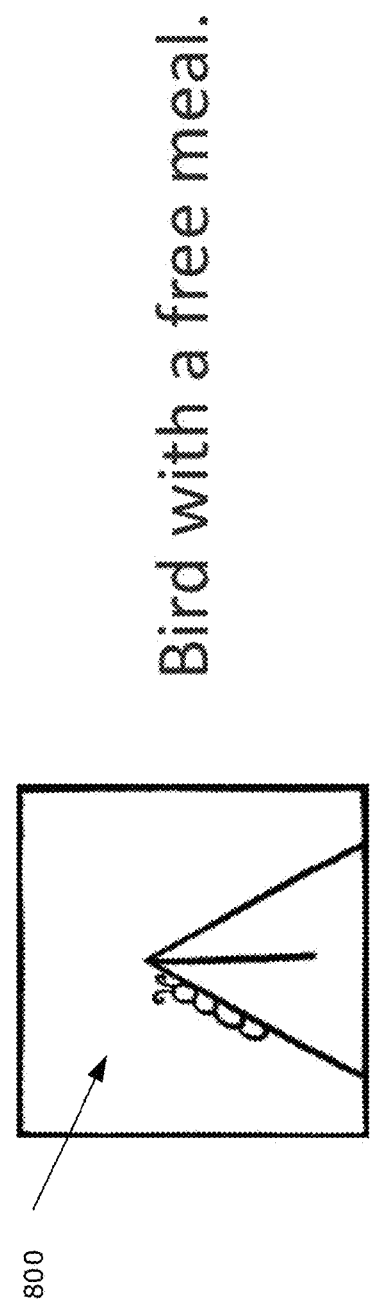
FIG. 8E is an example of an answer to the question posed in FIG. 8D, in accordance with examples of the present disclosure.
Figure 8F:
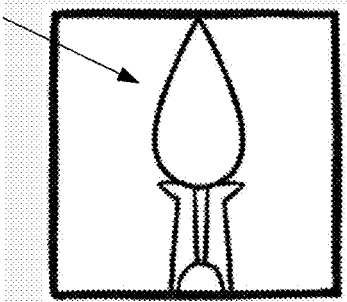
FIG. 8F is an example of a wellness content item, in accordance with examples of the present disclosure.
Figure 8G:
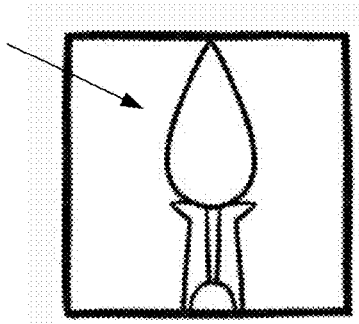
FIG. 8G is an example of an answer to the question posed in FIG. 8F, in accordance with examples of the present disclosure.
Figure 8I:
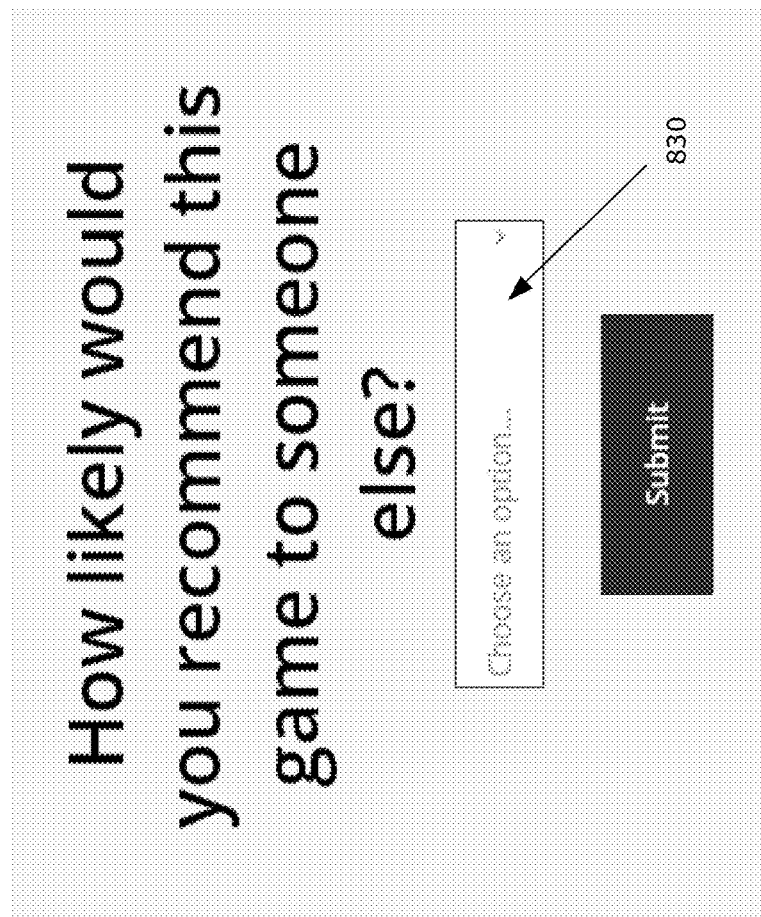
FIGS. 8H and 8I show examples of a "check-in prompt" that may be served to a user engaging with the digital wellness platform, in accordance with examples of the present disclosure.
Figure 8H:
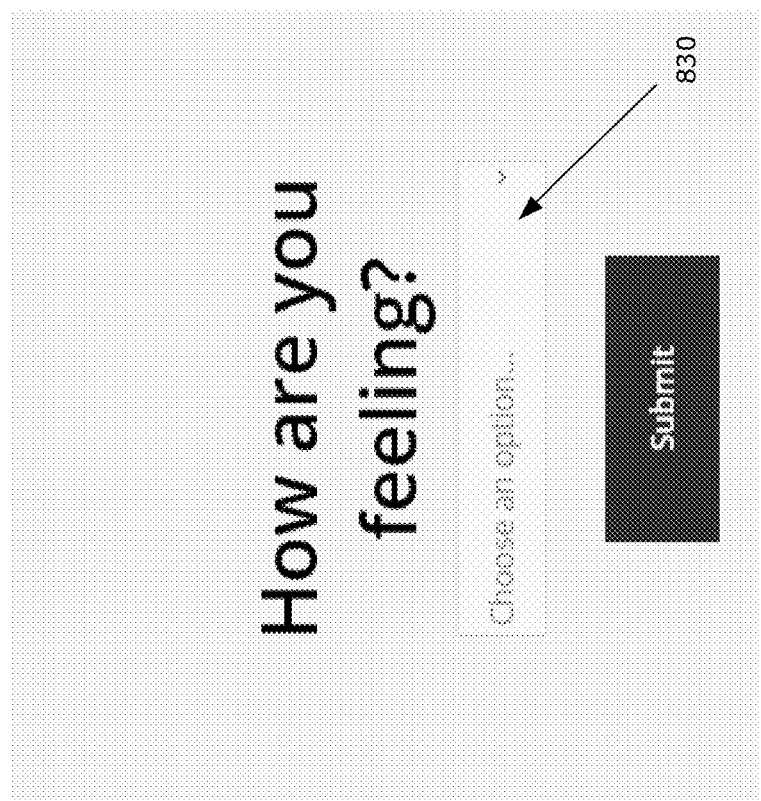
Figure 8J:
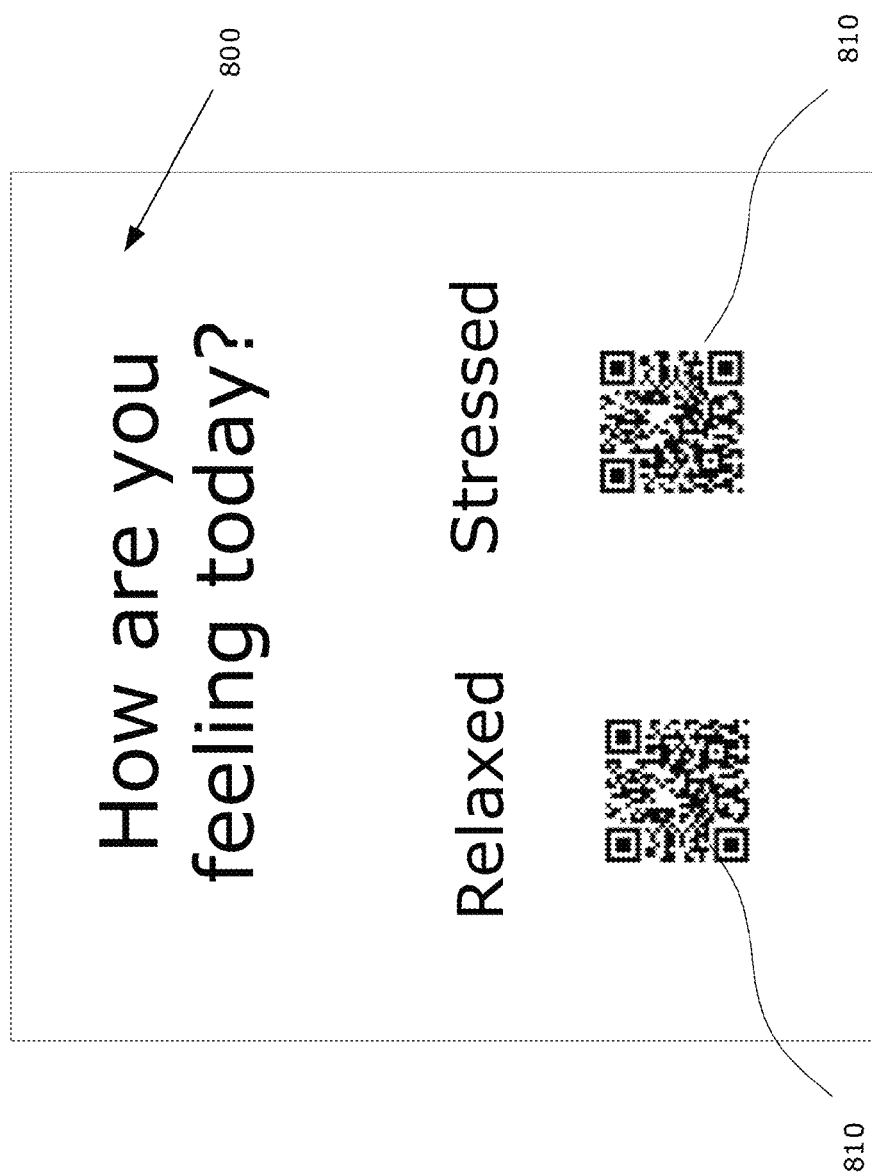
FIG. 8J is an example of a wellness content item made available in public spaces and having one or more associated QR codes, in accordance with an example embodiment of the present disclosure.

In examples, an analytics dashboard 390 may also analyze mood record data stored in the mood record database 150 and display information in a dashboard user interface 395, as described with respect to FIG. 8J

In examples, the digital content delivery system 300 employs several models of content delivery. In one embodiment, a user or a user's employer may subscribe to a digital wellness service associated with the digital content delivery system 300 and the user may receive a personalized communication (e.g. email) to remind and invite the user to engage with wellness content items on the digital wellness platform. Although the present disclosure describes some examples in the context of receiving reminders and invitations to engage with the digital wellness platform via email applications, it should be understood that the present disclosure may encompass other forms of electronic messages (e.g., instant messaging, text, app notifications etc.).

Figure 7A:
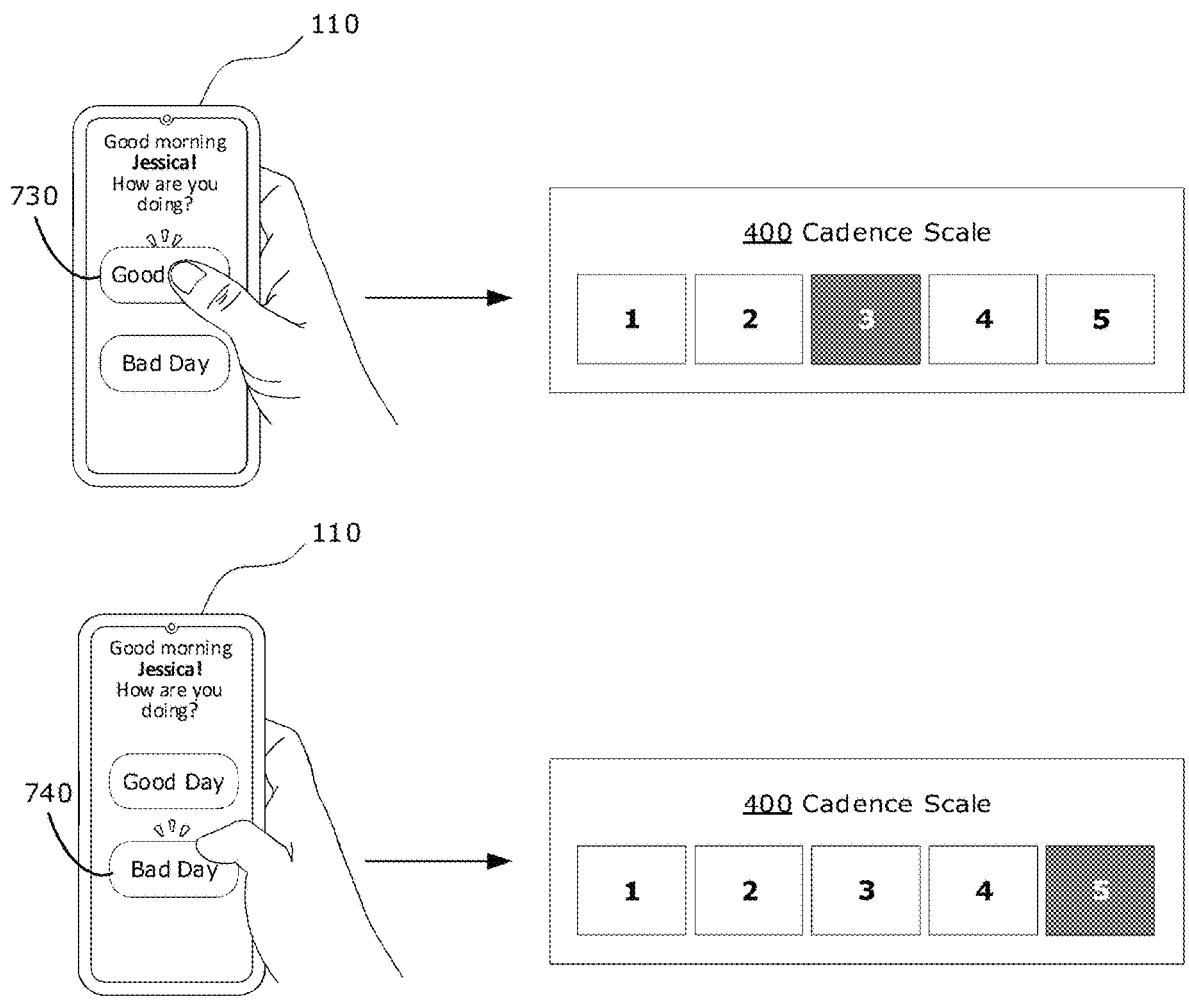
FIG. 7A is an example of a personalized email received by a user on a mobile communications device, in accordance with an embodiment of the present disclosure.

FIG. 7A shows an example of a personalized email received by a user on a mobile communications device, in accordance with an embodiment of the present disclosure. In examples, the user may open a personalized email on an electronic device (e.g. a smart phone, a tablet, a laptop etc.).

In examples, a personalized email may check-in on the user's emotional state by posing a question such as "How is your day going?" or by posing another question. In another example, if the user is attending a sporting event or is engaged in a gambling activity (e.g., sports gambling, or other gambling, such as in a casino or in an online sports betting or gambling platform, etc.) the personalized email may pose a question such as "How is your luck running today?", among others. In examples, the user may be provided with options to select "good day" 730 or "bad day" 740, for example, using a touchscreen, a stylus or a mouse etc., based on how they are feeling at the current time. In some embodiments, for example, selecting "good day" 730 may be mapped to a value of 3 on the cadence scale and selecting "bad day" 740 may be mapped to a value of 5 on the cadence scale. In other embodiments, for example, selecting "good day" 730 or "bad day" 740 may be mapped to another value on the cadence scale, a specific content type, a mood parameter 330 or another mapping, based on user history on the digital content delivery system 300, prior interactions with wellness content or user preferences.

Figure 7B:
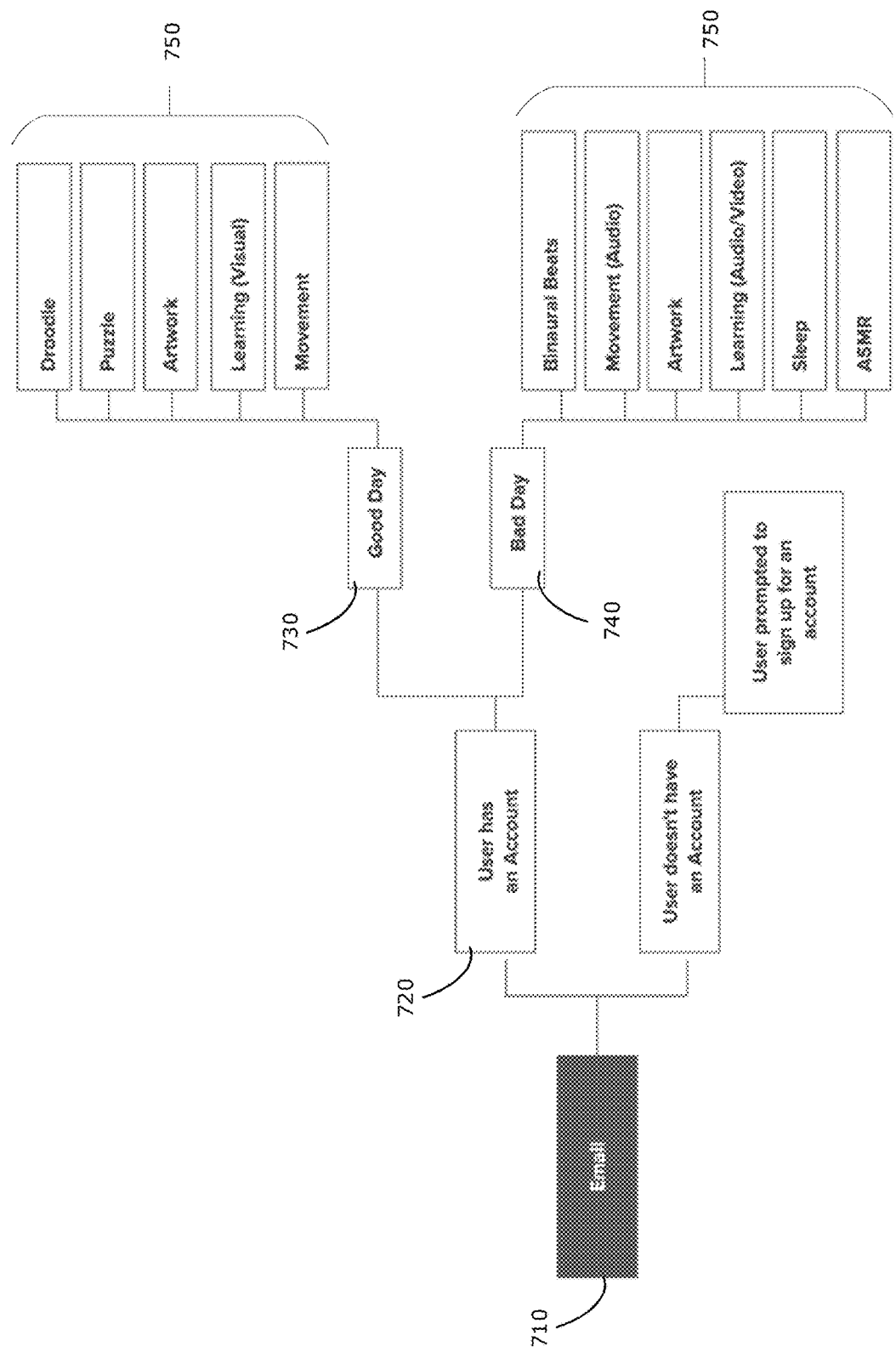
FIG. 7B is an example workflow of the email delivery model for serving wellness content to a user, in accordance with an embodiment of the present disclosure.

FIG. 7B shows an example workflow of the email delivery model for serving wellness content to a user, in accordance with an embodiment of the present disclosure. In examples, a user receives an email 710 including a first question posed to the user. In response to submitting an answer to the posed question, the digital content delivery system 300 may be launched on the user's electronic device and the user may be prompted to sign in to their account 720 for accessing the digital content delivery system 300. In examples, once a user account has been authenticated, the user may be presented with a personalized dashboard showcasing one or more recommended wellness content items 750 to engage with, based on the user's assigned mood parameter 330. Optionally, the user may also be presented with one or more recommended wellness content items 750 based on prior engagement history with wellness content, or based on other factors including the time of day or the user's location.

In examples, the selection of "good day" 730 or "bad day" 740 in the personalized email may initiate the creation of a mood record 350 for the user and a respective mood parameter 330 may be assigned to the user and stored in the mood record 350.

In some examples, engaging with the recommended wellness content item(s) 750 or another wellness content item(s) may induce a "good day response" in the user. For example, engaging with the wellness content may help to shift the user's brain from a stressed state to a more relaxed state. The change in the user's emotional state may be detected based on explicit user input (e.g. the user interacts with a UI to select a "good day", after engaging with the wellness content) and/or may be detected based on implicit user interactions with the system 300 (e.g. the user repeatedly engages with the same wellness content, suggesting the user finds that wellness content to be beneficial to their emotional state). In some examples, the user may be guided through the wellness content in a specific order, for example, by showing "play" and "lock" icons on wellness content items that are available or unavailable, respectively. For example, the first wellness content item that is available may be considered as a "warm up", while the second wellness content item may be considered "training" and may be locked until the "warm up" video has been watched etc. In examples, the user may choose to engage with the recommended wellness content 750 or the user may navigate to other wellness content on the digital content delivery system 300. User engagement with wellness content may be tracked through a user account and wellness statistics may be tracked for each user over time, for example, to track the number of "good days" vs. the number of "bad days" and observe any improvements. In examples, a user may receive one or more emails a week, for example, three emails each week to prompt user engagement with the wellness content on the digital wellness platform. In some embodiments, for example, the user may accumulate reward points for each video watched or task performed and may spend the accumulated reward points on prizes or other rewards within the digital content delivery system 300. In examples, accumulated user reward point totals may be displayed on a leader board within the user interface (e.g., the digital wellness platform) and users may earn badges or other awards based on the accumulated reward points.

Figure 7C:
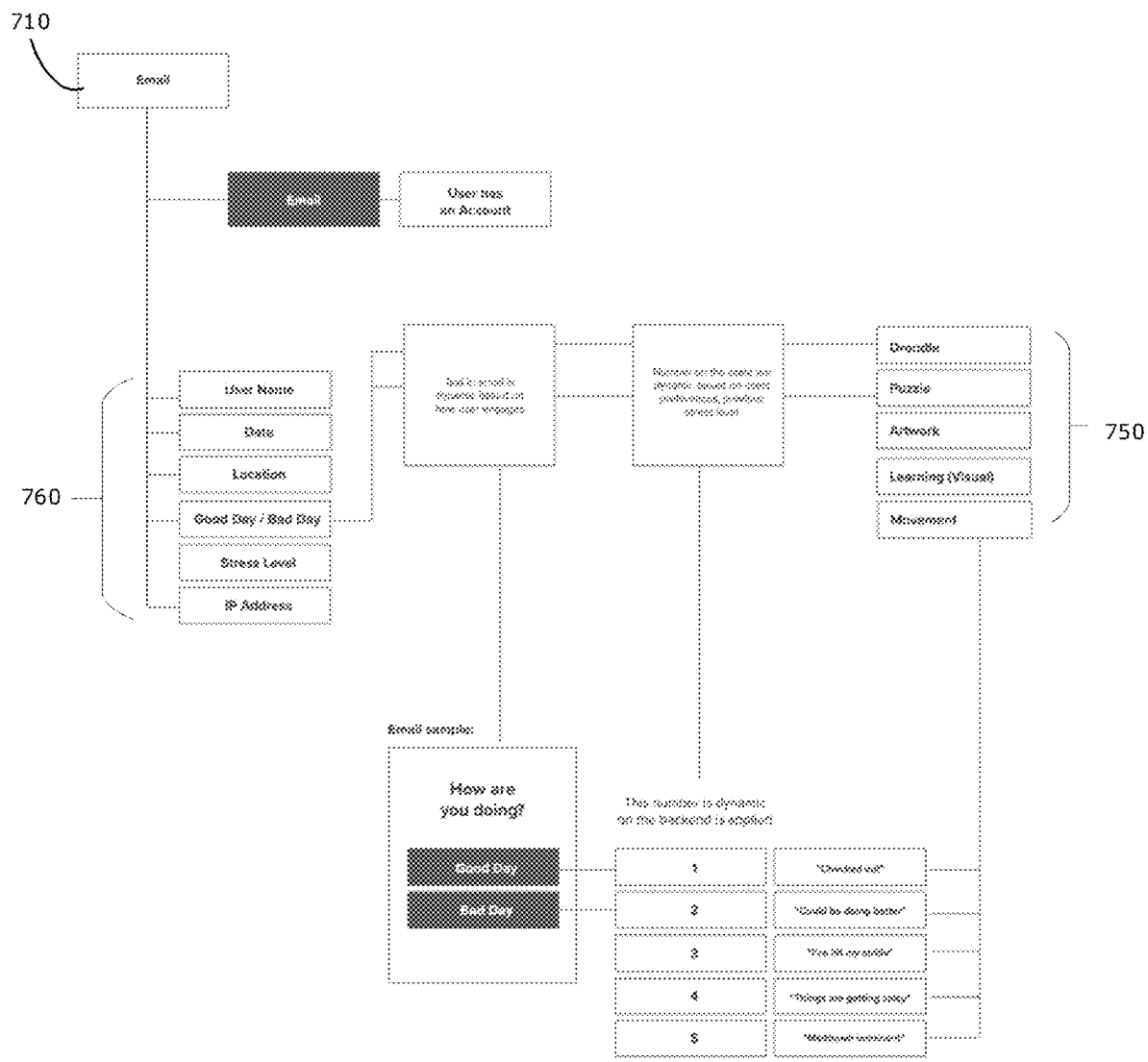
FIG. 7C is an example workflow of the email delivery model for serving wellness content to a user, in accordance with another embodiment of the present disclosure.

FIG. 7C shows an example workflow of the email delivery model for serving wellness content to a user, in accordance with another embodiment of the present disclosure. In some examples, a user behavior where the user engages with a personalized email may cause the collection of additional email interaction data 760, for example, data related to clicking behavior, number or frequency in which the email is opened, user name, date/time, location or bounce rate, "good day"/"bad day" response, stress level, IP address, among other data related to user engagement with the personalized email (which may be subject to the user's consent). In examples, collection of additional email interaction data may or may not be associated with the user account, and may be stored in a database of the digital content delivery system 300 and may be used to dynamically serve text to the user in an email, based on the past user engagement, and/or dynamically map a "good day" 730 or "bad day" 740 response to a number on the cadence scale 400 for serving recommended wellness content 750.

In other embodiments, for example, a service provider (e.g., an airport, an entertainment complex, a medical facility, a casino or an online gambling platform, etc.) may subscribe to a digital wellness service associated with the digital content delivery system 300 and wellness content may be delivered to a plurality of users in a collective setting or a public space, for example, in a waiting room, in an airport lounge, a concession area, or an online or offline gambling environment, among others.

FIGS. 8A and 8B are examples of wellness content 800 made available in public spaces for collective access and benefit in accordance with an example embodiment of the present disclosure. For example, FIG. 8A is an example of wellness content 800 on one or more wall-mounted screens in a bar or restaurant (e.g., in an airport lounge, casino or concession area, etc.) and FIG. 8B is an example of wellness content 800 on one or more wall-mounted screens in a hallway (e.g., an airport walkway or passenger boarding bridge). In other examples, wellness content or an associated QR code may be made available in public spaces on electronic devices (e.g., on a tablet device or a kiosk, among others) or in the form of stickers, decals or signs, for example, affixed to a seat in a stadium, or on a gaming terminal or slot machine in a casino, among others. In examples, a user in a public space may be presented with a wellness content item (e.g. a Droodle™ or an artwork etc.) or a teaser for a digital wellness content item (e.g. a question prompting the user to engage with the wellness content) in the collective setting or public space. In examples, the wellness content item may be paired with an associated QR code 810, and may also include text inviting the user to use the QR code 810 to interact with the wellness content item. In examples, the QR code 810 may be scanned or opened with an electronic device (e.g. smartphone, tablet etc. having a camera application that enables scanning of QR codes or a QR code scanning application) to interact with the wellness content item on the digital wellness platform. In examples, the QR code 810 may present a digital wellness content item, for example, an image or a video, to the user via their electronic device and may enable the user to interact with the digital wellness system and associated wellness content via a user interface on the user's electronic device.

FIG. 8C is an example of a wellness content 800 with an associated QR code 810 being scanned by a camera application on an electronic device, in accordance with an example embodiment of the present disclosure. For example, if the wellness content item is a Droodle™, the user may be prompted to enter an answer to a question regarding the Droodle™ image (e.g. "what do you think I am . . . ") and the user may then view other responses from other users to the same question. In this way, the wellness content item may be an interactive digital content, rather than passive digital content (e.g. passively viewing a video or message). Further, the user may be able to view interactions from multiple other users. The system 300 may moderate or filter the responses from other users, to ensure that the user interaction serves to improve the user's emotional state. For example, the system 300 may only enable positive or neutral responses (e.g. determined based on semantic analysis of words used in the responses) to be viewed. In other examples, the system 300 may limit the responses that are displayed to a given user to only the responses obtained from other users sharing a common characteristic (e.g. same geographical location, same time period, same company, etc.). In some examples, the mood enhancing technology may induce a "good day response" in the user. For example, interacting with the wellness content item or another wellness content item(s) may help to shift the user's brain from a stressed state to a more relaxed state. In this regard, the wellness content item visible in the collective setting or public setting has the opportunity to reach more than one user in a group of users simultaneously, and may help to collectively induce a "good day response" in the group of users or otherwise enhance the user's well-being by providing access to recommended digital wellness content tailored to their emotional state. In some embodiments, for example, within a casino setting, the utilization of QR codes within the casino environment may help promote responsible gambling. In examples, casino visitors can scan QR codes to access mood-enhancing content designed to foster positive play behaviors and manage their emotional state while enjoying their favorite games.

FIG. 8D is an example of a wellness content 800 with an associated QR code 810, in accordance with examples of the present disclosure and FIG. 8E is an example of an answer to the question posed in the wellness content 800 of FIG. 8D, in accordance with examples of the present disclosure.

FIG. 8F is an example of a wellness content item 800, in accordance with examples of the present disclosure. In examples, in response to scanning a QR code 810, the wellness content 800 may be displayed in the digital wellness platform and, for example, a user may input (e.g., submit a "guess") an answer to the displayed Droodle™ or otherwise engage with another wellness content 800, for example, by entering text into a text box. In response to submitting a "guess", the digital wellness platform may provide the user with a correct answer, as shown in FIG. 8G. In examples, a user may also view a list of other submissions (or "guesses") made by other users associated with the same wellness content item, and users may score their answer, for example, by selecting "close enough" if their answer was correct and "not even close" if their answer was incorrect, in order to progress to the next wellness content 800 (e.g., another puzzle).

FIGS. 8H and 8I show examples of a "check-in prompt" that may be served to a user engaging with the digital wellness platform, in accordance with examples of the present disclosure. For example, FIG. 8H enables a user to select from a list of options that describes how they are feeling, for example, "happy", "content", "bored/stressed", "annoyed" or "stressed", among others while FIG. 8I provides an example of a net promotor score (NPS) prompt. A NPS may represent how likely a user is to recommend the digital wellness platform to someone. As such, the NPS may be another indicator of how the user's emotional state when the user engages with the digital wellness platform.

In other examples, an online gambling platform may subscribe to a digital wellness service associated with the digital content delivery system 300 and may prompt the player to check-in after a certain duration of online play, for example, using an API for enabling the exchange of information between the online gambling platform and the digital wellness platform. In examples, this check-in prompt may pose questions such as "How's your luck today?" or "Rate your recent bets" to gauge the player's emotional state and provide relevant mood-enhancing content accordingly. In an example, a user who is increasingly interacting with an online gaming or sports betting platform may find that over time, unsuccessful bets or losses lead to feelings of isolation, frustration and loneliness, and a craving for more gambling wins as a source of excitement and connection. In examples, the digital content delivery system 300 may push a check-in prompt to the user within the online gaming or gambling platform, for tracking the user's mood while playing with tailored activities. In examples, an initial mood for the user may be benchmarked at the beginning of a playing session, and one or more check-in prompts may be served to the user at custom time intervals, among others. For example, a check-in prompt asking the user to "Rate your recent bets" may provide the user with a set of responses including "tough break", "steady hand", "betting bliss", "winning streak" or "jackpot joy", among others, where each selection from the set of responses is associated with an emotional state. In examples, a recommended wellness content item 750 may be served to the user based on the selected response, for causing a mood enhancing response in the user and promoting responsible and/or safer gaming practices.

In some embodiments, for example, a check-in prompt, an NPS prompt or another type of prompt may serve as a feedback prompt, for gathering feedback on user satisfaction with the mood enhancing technology (e.g., the wellness content items, the wellness content platform, the frequency of check-in prompts, the content delivery method, among others), or alternatively, for gathering feedback on the efficacy of wellness interventions, for example, as related to a user's current emotional state or changes in a user's emotional state. In examples, feedback obtained through a feedback prompt may be used to fine-tune the recommendation engine 360 or the feedback may be analyzed internally by organizations such as airports, medical facilities, educational institutions, sports and entertainment venues, casinos etc. for informing decisions about the well-being of visitors or employees.

In some embodiments, for example, QR codes may be strategically placed within advertisements, for example, in print or digital media, for providing entry points to a personalized digital wellness experience. For example, users encountering QR codes within advertisements can access mood-enhancing content relevant to their emotional state, thereby promoting a positive mental state while engaging with advertisements.

FIG. 8J is an example of a wellness content 800 made available in public spaces and having one or more associated QR codes 810, in accordance with an example embodiment of the present disclosure. In examples, the wellness content 800 may pose a question or check-in prompt to engage the user (e.g., how are you feeling today?) and may provide one or more QR codes 810 for the user to scan. In examples, each of the provided QR codes 810 may be associated with an emotional state, for example, "relaxed" or "stressed", among others, to guide the user in scanning an appropriate QR code reflecting their emotional state. In examples, a user may be served a custom digital wellness content item based on their selection of QR code scanned, for example, if the user scans the QR code associated with a "stressed" emotional state, the user may be served a digital wellness content item with the goal of improving the user's emotional state. In examples, if the user scans the QR code associated with a "relaxed" emotional state, the user may be served a digital wellness content item with the goal of maintaining the user's emotional state.

Figure 8K:
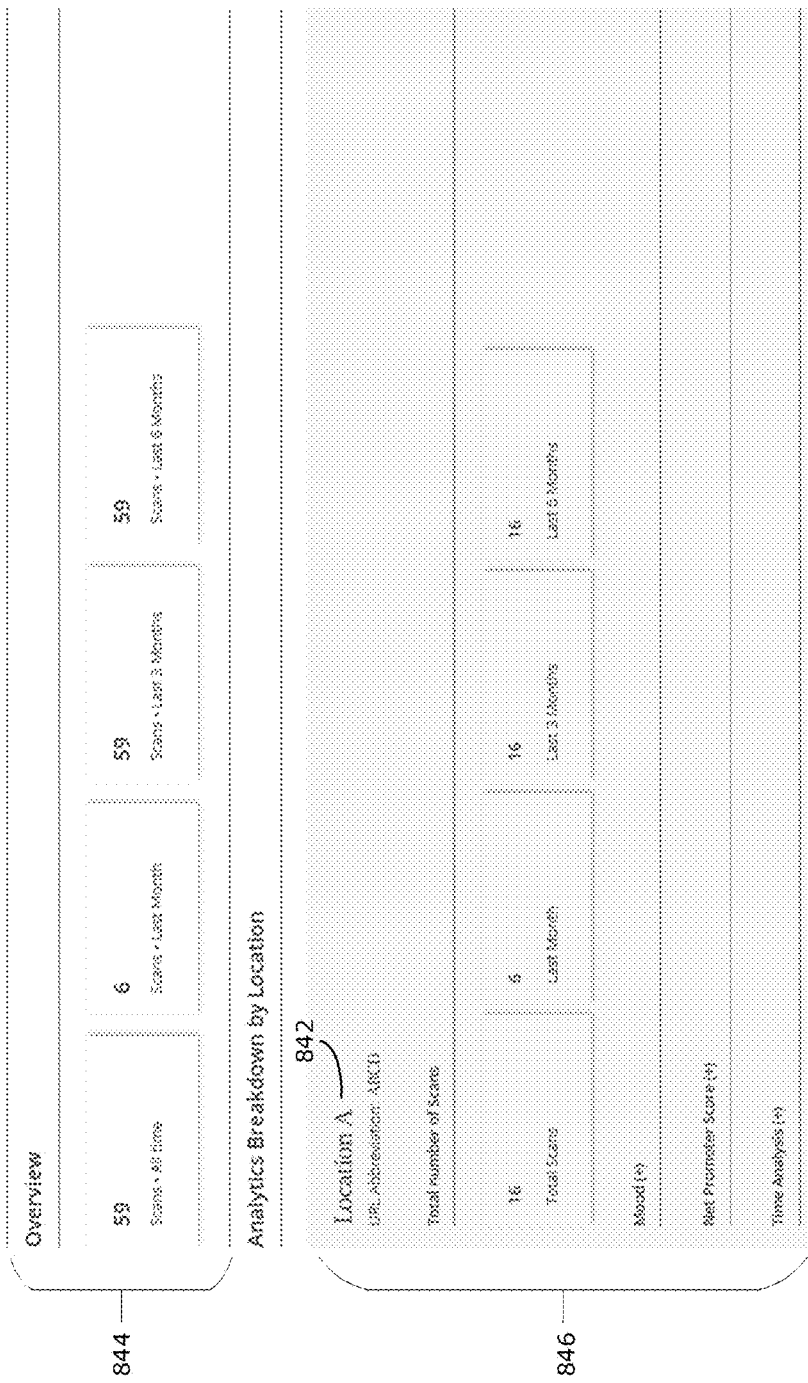
FIG. 8K is an example analytics dashboard, in accordance with examples of the present disclosure.

FIG. 8K is an example analytics dashboard 390, in accordance with examples of the present disclosure. For example, the analytics dashboard 390 may be used to analyze and communicate user interaction data collected for one or more public digital wellness content items within a public space 840, such as an airport, a stadium, a hospital etc., or at discrete locations 842 within the public space 840, using public digital wellness content items accessible at predetermined locations throughout the public space, for example, within an Airport, one or more predetermined locations 842 may include domestic baggage, security (e.g., TSA), or customs, etc.

For example, user interaction data may be generated by tracking the number of users who scan a QR code, the time spent interacting with the digital wellness content, the NPS and/or the types of interactions (such as viewing videos, reading articles, or completing surveys), among others. In examples, statistics may be displayed in an overview panel 844, for example, showing the total number of times that one or more public digital wellness content items have been accessed for various time periods, such as "all time", "last month", "last 3 months" or "last 6 months", among others. In examples, user interaction data may be analyzed for each predetermined location 842 within the public space 840, for example, in a location panel 846, to provide information on user engagement in the location, to provide information on the mood of users in these locations, using tools such as the cadence scale or net promotor score, etc. In examples, time-based analytics may also be available, in addition to location-based analytics. In this regard, operators of a public space 840 may identify patterns and trends in user behavior, such as which types of content are most popular or which areas of the airport see the highest engagement with the QR codes, or may observe trends related to user mood or stress level and may be able to take action in response to observed behavioral indicators, for example, to help improve the mood and/or stress level of individuals occupying these locations. Further, the analysis of user interaction data may provide insights into the effectiveness of wellness QR codes in different areas of the airport. For example, comparing the engagement and impact of QR codes located in domestic baggage versus customs areas may indicate which areas are more effective in promoting wellness among travelers. In other examples, analyzing user interaction data may indicate which types of content are most engaging and effective in promoting wellness, such that operators of a facility may adjust the content accordingly to improve the user experience. In examples, the analytics dashboard 390 may be customizable. In examples, an "add location" button 848 may enable users to add a location panel 846 corresponding to one or more predetermined locations 842 to the analytics dashboard user interface.

Figure 8L:
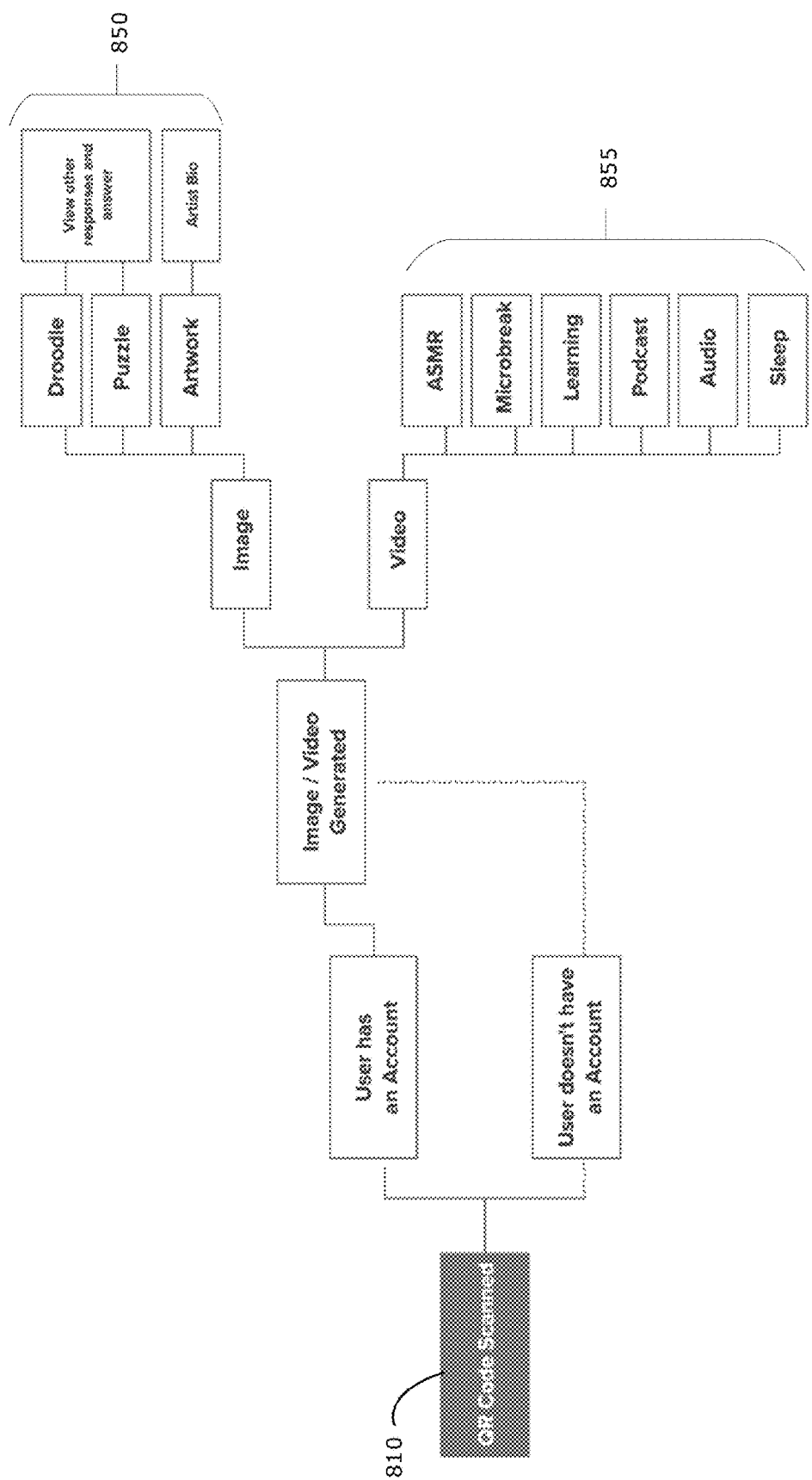
FIG. 8L is an example workflow of the QR delivery model for serving wellness content to a user, in accordance with an example embodiment of the present disclosure.

FIG. 8L shows an example workflow of the QR delivery model for serving wellness content to a user, in accordance with an example embodiment of the present disclosure. In examples, a user may scan a QR code 810 to initiate interacting with digital wellness content. if the user or the user's employer is a subscriber of a digital wellness service or already has a user account on the digital wellness platform the user may be prompted to log in with their user account credentials, or they may be automatically logged in on their electronic device. Alternately, if a user or a user's employer is not a subscriber of a digital wellness service they may be prompted to create a user account, or if the user wishes to remain anonymous, the user may begin interacting with the digital wellness content item associated with the QR code 810 through a user interface on the user's electronic device. In examples, the digital wellness content item may be an image 850 (e.g., a Droodle™, a puzzle, an artwork etc.) or the digital wellness content item may be an audio/video content 855 (e.g., ASMR, microbreak, learning, podcast, audio, sleep training etc.).

In some examples, a user behavior where the user engages with a wellness content using a QR code 810 may cause the collection of additional QR code interaction data (which may be subject to the user's consent), for example, data related to the number of times the wellness content is accessed or opened, time, location, bounce rate, and the number of times artist profiles are viewed, among other data related to user engagement with the QR code 810. In examples, collection of additional QR code interaction data may or may not be associated with the user account, and may be stored in a database of the digital content delivery system 300.

Figure 8M:
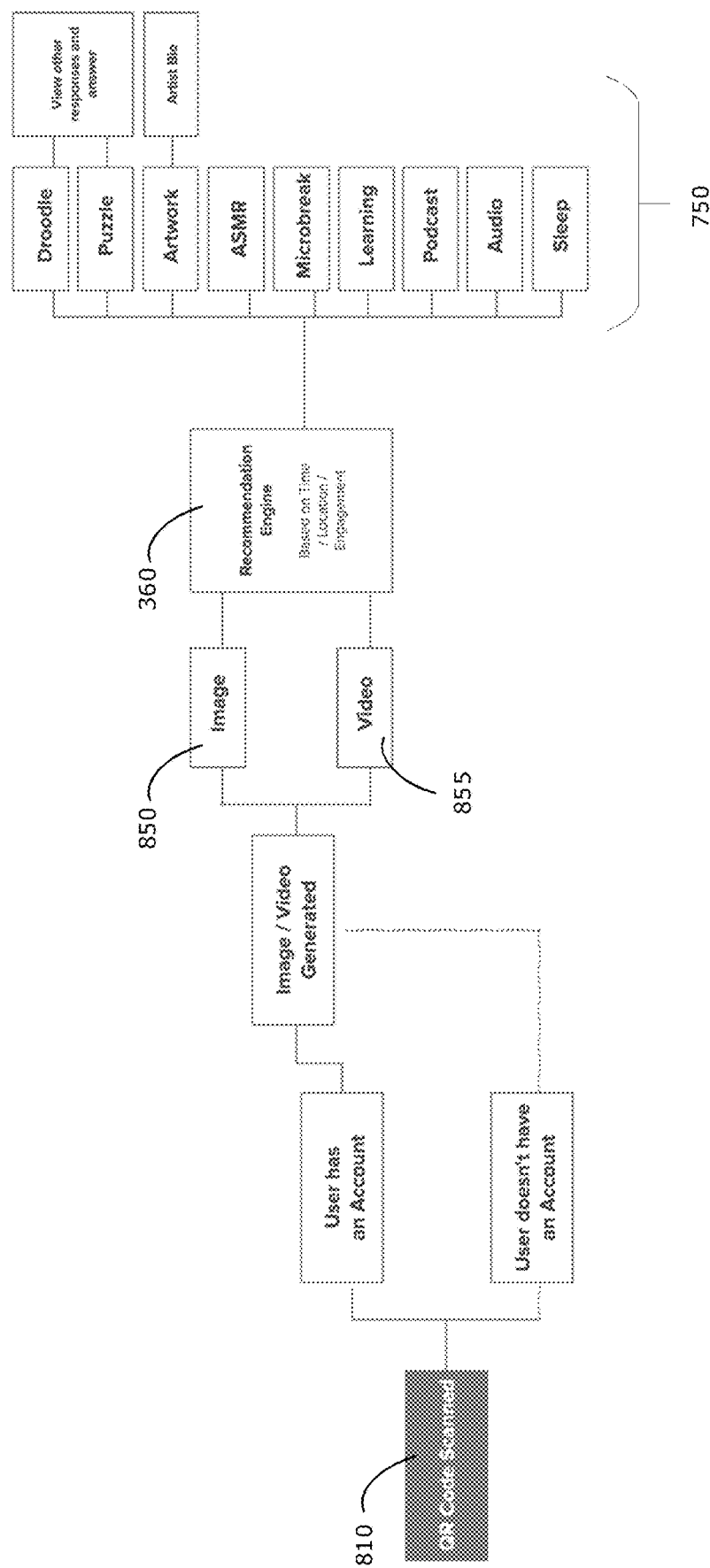
FIG. 8M is an example workflow of the QR delivery model for serving recommended wellness content to a user, in accordance with an example embodiment of the present disclosure.

FIG. 8M shows an example workflow of the QR delivery model for serving recommended wellness content to a user, in accordance with an example embodiment of the present disclosure. In examples, a user may scan a QR code 810 to initiate interacting with digital wellness content. In examples, regardless of whether the user has a user account, an image 850 or an audio/video content 855 may be presented to the user in response to scanning the QR code. In response to the user interaction with either the image 850 or the audio/video content 855, recommendation engine 360 may receive the user interaction and may generate a recommended wellness content 750 to provide to the user for further engagement, based on a user's engagement with the image 850 or the audio/video content 855.

In some embodiments, for example, the digital wellness content may be delivered to users (e.g., fans) in a stadium, a sports arena or a concert venue during a sporting event or a concert, among other events, to enhance the user's experience during waiting periods and/or to provide feedback to facility operators related to customer satisfaction. For example, digital wellness content may be customized to appeal to fans of specific sports teams or entertainers, for example, by introducing or incorporating games, quizzes or fan trivia elements to digital wellness content items. In examples, users may be required to wait during a break in game play, during an intermission, between performers/acts, in concession areas, or in other lines. In examples, users may engage with digital wellness content while they are waiting, by scanning a QR code 810 in a predetermined location 842 within the sporting or concert venue. In some embodiments, the QR code may be provided on a wall, on a screen, or on a seat in the predetermined location 842, to engage users while they are waiting. In other embodiments, the QR code may be provided to a user on a tablet or another device by an employee of the sporting or concert venue or by another individual in the predetermined location 842, to engage users while they are waiting, for example, while waiting for food, beverage and/or merchandise purchases in the concession area. In other examples, digital wellness content may be served to users (e.g., players) of an online gaming platform in the form of a series of quiz questions during live breaks, for example, offering a more engaging experience. In examples, users participating in games, quizzes or fan trivia may accumulate points that can be redeemed for prizes or other rewards, contributing to a more enjoyable and rewarding gaming experience.

In examples, user interaction data gathered from one or more predetermined locations may be analyzed and presented in real-time in an analytics dashboard 390, for example, for operators of the sporting or concert venue to monitor user sentiment or mood in real-time. In examples, operators of the sporting or concert venue may respond to changes in fan sentiment or mood, based on the user interaction data, for example, to improve user experience and/or respond to user needs and preferences.

In some embodiments, the digital wellness content provided to fans at a sporting or concert venue may be tailored to a unique sport, team or performer, (e.g., a football team, a singer, etc.) to correspond to a particular event taking place at the stadium, sports arena or concert venue. In some embodiments, for example, users who engage with digital wellness content during a sporting event or concert may receive a communication after the event thanking them for participating, and/or offering a special promotion or discount, for example, for future events or purchases at the sporting or concert venue, among others. In some examples, engagement with digital wellness content by users at sporting or concert venues may enhance fan relationships with certain sports, teams or performers, and may help to foster brand loyalty.

In another embodiment, the digital wellness content may be delivered to a personalized electronic device within a collective setting, for example, a screen in an airplane. In another embodiment, the digital wellness content may be delivered to a personalized electronic device within a public setting, for example, on a user device 110 in a hospital waiting room or another waiting room, or another public setting. In another embodiment, the digital wellness content is delivered as audio content, for example, binaural audio delivered to a user while they are waiting for service, for example, while waiting on hold on the phone. In examples, the type of binaural audio content that is served to the user may depend on the current emotional state of the user (which may be explicitly indicated by the user, for example by selecting one of multiple options presented via interactive voice response (IVR)). For example, all music may feel similar and have a melodic and tonal through line, the video's relationship to a user's emotional state or a position on the cadence scale may dictate the tempo and corresponding binaural beats embedded within the music. For instance, videos associated with emotional states at the high end of the cadence scale (approaching burnout) may be slower and feature binaural beats that induce a meditative Theta state, while a video associated with emotional states on the low end of the cadence scale may feature beats that promote a Beta state for motivation.

Figure 9:
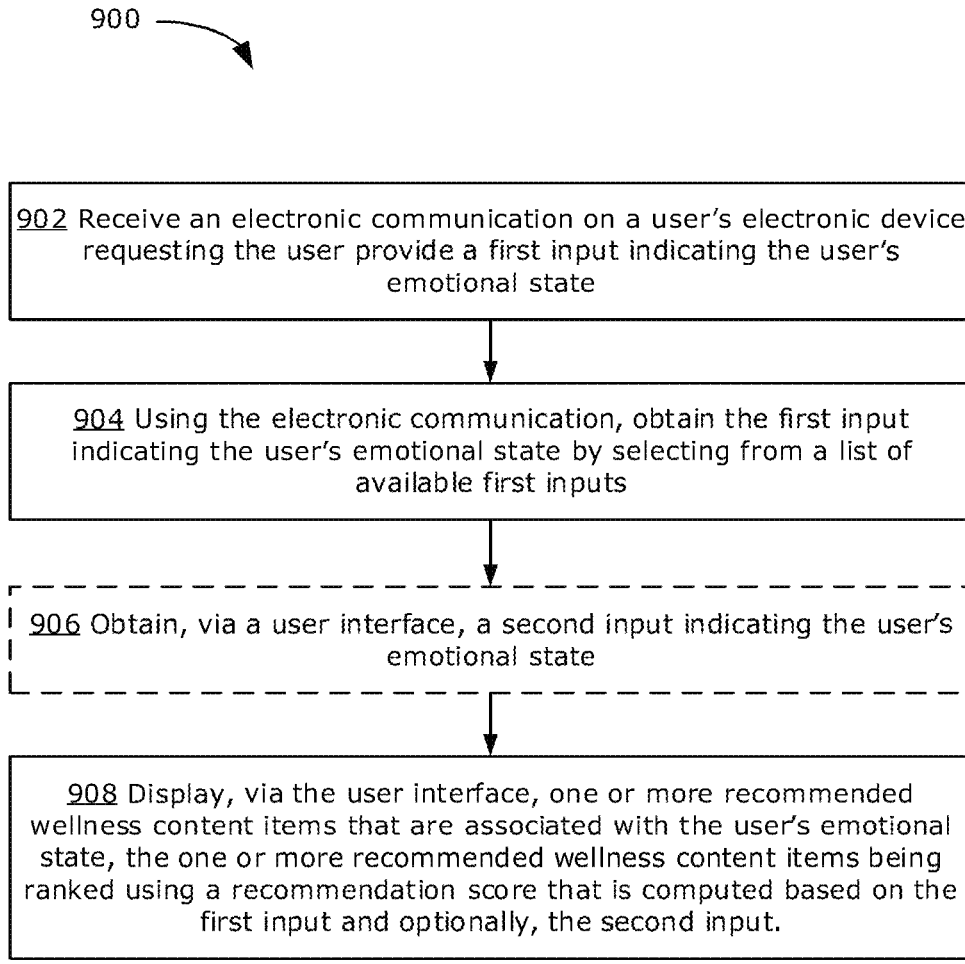
FIG. 9 a flowchart illustrating an example method at an electronic device, for receiving a recommended digital wellness content responsive to a user's emotional state, in accordance with an example embodiment of the present disclosure.

FIG. 9 is a flowchart illustrating an example method at an electronic device, for receiving a recommended digital wellness content responsive to a user's emotional state, in accordance with an example embodiment of the present disclosure.

Method 900 begins with step 902 in which a user receives an electronic communication on the user's electronic device requesting the user provide a first input indicating the user's emotional state. In examples, the electronic communication may be an email or another form of electronic communication.

At step 904, the first input indicating the user's emotional state is obtained by receiving a selection of the first input from a list of available first inputs in the electronic communication. For example, the body of the email message may include one or more selectable first inputs as buttons or images with associated hyperlinks, and a user may click on the button or image to select the first input, for example, clicking on a button. In examples, the list of selectable first inputs representing the user's emotional state may be one of a "good day" input or a "bad day" input and may be selected in response to a question posed to the user in the body of the email, for example, "how is your day going?". In another example, the first input may include an emotional check-in prompt, for example, by posing a question such as "how are you feeling?", "how is your luck running today?" or "how well is your team playing today?" or an NPS prompt, among other ways of capturing a user's emotional state.

Optionally, at step 906 a second input indicating the user's emotional state may be obtained via a user interface on the electronic device. In examples, a second input may be a numeric representation of the user's stress level, for example, on the cadence scale of 1-5 or the second input may be another input.

At step 908, one or more recommended wellness content items that are associated with the user's emotional state may be displayed to the user via the user interface. In examples, the one or more recommended wellness content items may be ranked using a recommendation score that is computed based on the first input and optionally, the second input.

Figure 10:
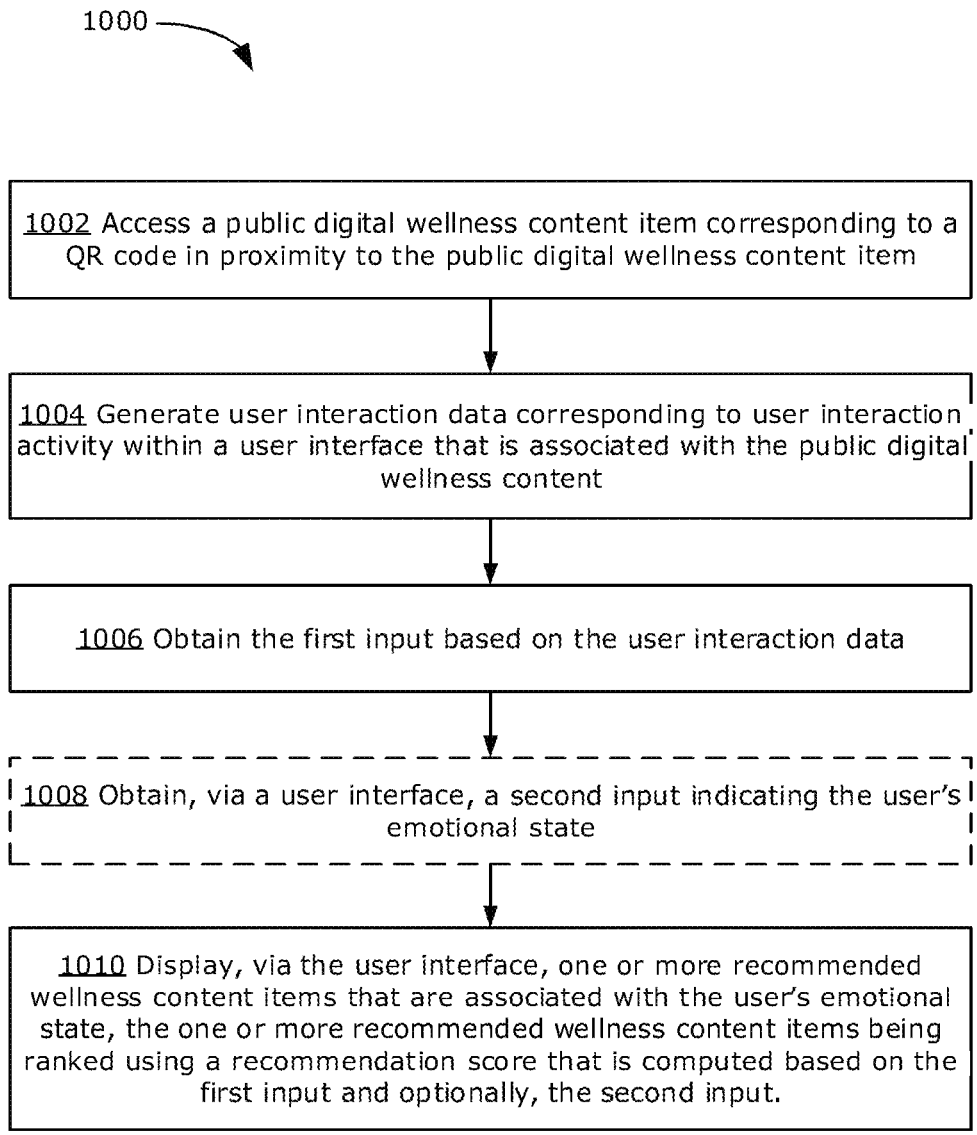
FIG. 10 a flowchart illustrating an example method at an electronic device, for receiving a recommended digital wellness content responsive to a user's emotional state, in accordance with an example embodiment of the present disclosure.

FIG. 10 is a flowchart illustrating an example method at an electronic device, for receiving a recommended digital wellness content responsive to a user's emotional state, in accordance with an example embodiment of the present disclosure.

Method 1000 begins with step 1002 in which a public digital wellness content item corresponding to a QR code 810 in proximity to the public digital wellness content item may be accessed. For example, the digital wellness content item corresponding to the QR code 810 may be opened in a user interface.

At step 1004, user interaction data associated with user interaction activity within the user interface that is associated with the public digital wellness content item via a user interface may be generated. In examples, user interaction data may be stored in the user history database 140.

At step 1006, the first input representative of the user's emotional state may be obtained based on the user interaction data associated with the public digital wellness content item.

Optionally, at step 1008, a second input indicating the user's emotional state may be obtained via a user interface on the electronic device. In examples, a second input may be a numeric representation of the user's stress level, for example, on the cadence scale of 1-5 or the second input may be another input.

At step 1010, one or more recommended wellness content items that are associated with the user's emotional state may be displayed via the user interface. In examples, the one or more recommended wellness content items may be ranked using a recommendation score that is computed based on the first input and optionally, the second input.

Figure 11:
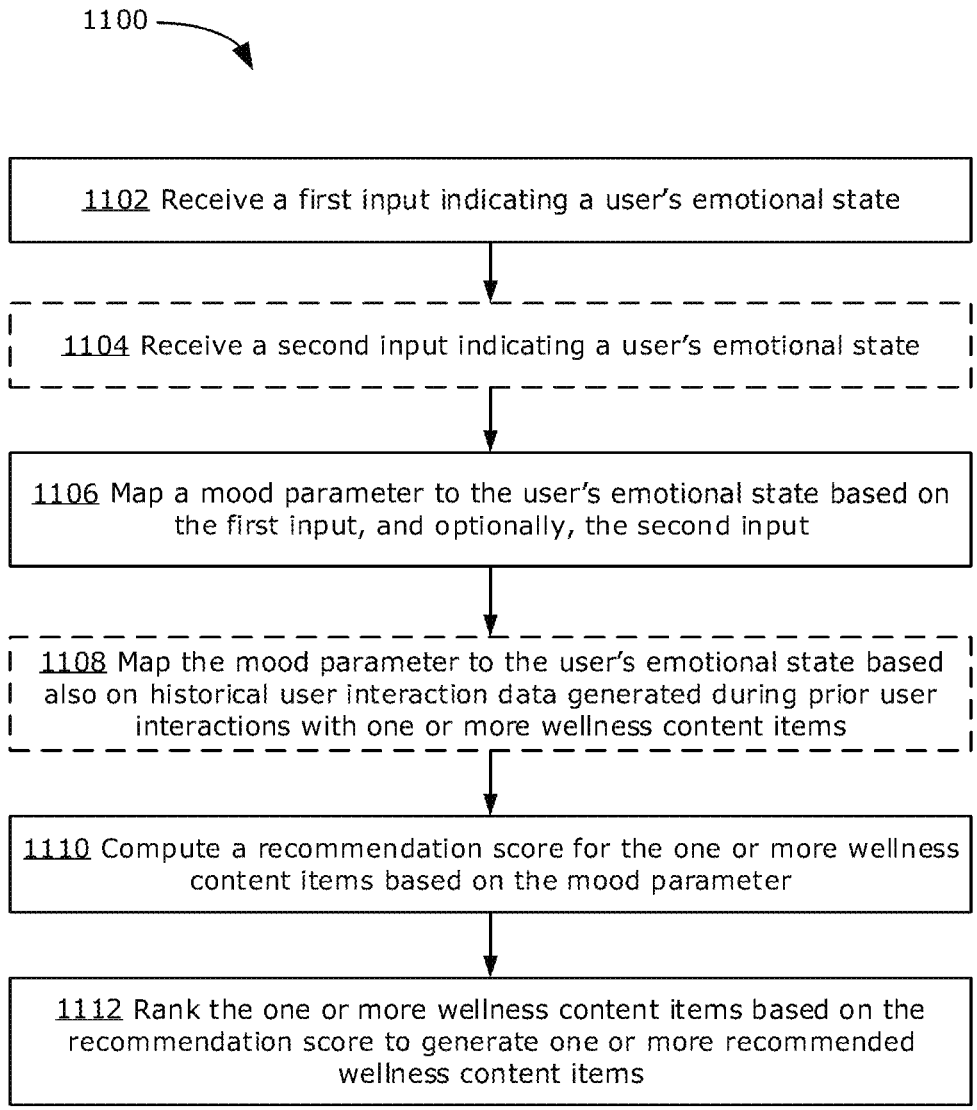
FIG. 11 a flowchart illustrating an example method at a wellness content server, for generating a recommended digital wellness content responsive to a user's emotional state, in accordance with examples of the present disclosure.

FIG. 11 is a flowchart illustrating an example method at a wellness content server, for generating a recommended digital wellness content responsive to a user's emotional state, in accordance with examples of the present disclosure.

Method 1100 begins with step 1102 in which a first input indicating a user's emotional state may be received by a wellness content server.

Optionally, at step 1104 a second input indicating the user's emotional state may be received by the wellness content server.

At step 1106, a mood parameter may be mapped to the user's emotional state based on the first input and optionally, also based on the second input.

Optionally, at step 1108, the mood parameter may also be mapped to the user's emotional state based on historical interaction data generated during prior user interactions with one or more wellness content items.

At 1110, a recommendation score may be computed for the one or more wellness content items based on the mood parameter.

At step 1112, the one or more wellness content items may be ranked based on the recommendation score to generate one or more recommended wellness content items.

Although some examples have been described in the context of a handheld electronic device (e.g., a smartphone), it should be understood that examples of the present disclosure may be implemented using other electronic devices, such as electronic wearable devices including laptop computers, tablets, desktop computers, smart appliances, wearable devices, assistive technology devices, virtual reality devices, augmented reality devices, Internet of Things (IoT) devices and interactive kiosks, among others.

Although the present disclosure describes methods and processes with steps in a certain order, one or more steps of the methods and processes may be omitted or altered as appropriate. One or more steps may take place in an order other than that in which they are described, as appropriate.

Although the present disclosure is described, at least in part, in terms of methods, a person of ordinary skill in the art will understand that the present disclosure is also directed to the various components for performing at least some of the aspects and features of the described methods, be it by way of hardware components, software or any combination of the two. Accordingly, the technical solution of the present disclosure may be embodied in the form of a software product. A suitable software product may be stored in a pre-recorded storage device or other similar non-volatile or non-transitory computer readable medium, including DVDs, CD-ROMs, USB flash disk, a removable hard disk, or other storage media, for example. The software product includes instructions tangibly stored thereon that enable an electronic device (e.g., a personal computer, a server, or a network device) to execute examples of the methods disclosed herein.

The present disclosure may be embodied in other specific forms without departing from the subject matter of the claims. The described example embodiments are to be considered in all respects as being only illustrative and not restrictive. Selected features from one or more of the above-described embodiments may be combined to create alternative embodiments not explicitly described, features suitable for such combinations being understood within the scope of this disclosure.

All values and sub-ranges within disclosed ranges are also disclosed. Also, although the systems, devices and processes disclosed and shown herein may comprise a specific number of elements/components, the systems, devices and assemblies could be modified to include additional or fewer of such elements/components. For example, although any of the elements/components disclosed may be referenced as being singular, the embodiments disclosed herein could be modified to include a plurality of such elements/components. The subject matter described herein intends to cover and embrace all suitable changes in technology.

The invention claimed is:

1. A method at an electronic device, comprising:
    accessing a first digital wellness content item corresponding to a QR code at a predetermined physical location, the first digital wellness content item being accessed by scanning the QR code using a camera associated with the electronic device;
    responsive to detecting user interaction activity associated with the first digital wellness content item, obtaining a first indication of a user's emotional state and location data corresponding to the predetermined physical location of the QR code and associated with the user interaction activity; and
    outputting, via a user interface for interacting with digital wellness content, one or more recommended wellness content items that are associated with the user's emotional state, the one or more recommended wellness content items being ranked using a recommendation score that is computed based on user interaction data including the first indication and the location data, with effect that the outputted one or more recommended wellness content items causes a positive emotional response in the user.

2. The method of claim 1, further comprising:
    obtaining, via the user interface, a second indication of the user's emotional state; and
    displaying, via the user interface, the one or more recommended wellness content items that are associated with the user's emotional state, the one or more recommended wellness content items being ranked using the recommendation score that is computed based also on the second indication.

3. The method of claim 1, wherein obtaining the first indication comprises one of:
    selecting a "good day" indication via the user interface;
    selecting a "bad day" indication via the user interface;
    selecting from a list of available first indications associated with a check-in prompt via the user interface;
    selecting from a list of available first indications associated with a net promotor score (NPS) via the user interface; or
    selecting from a list of available first indications associated with a feedback prompt via the user interface.

4. A method at a wellness content server, the method comprising:
    receiving an indication of user interaction activity associated with a first digital wellness content item corresponding to a QR code at a predetermined physical location and being accessed by a user by scanning the QR code using a camera associated with an electronic device;
    generating user interaction data for the first digital wellness content item, based on the user interaction activity, the user interaction data including a first indication of a user's emotional state and location data corresponding to the predetermined physical location of the QR code and associated with the user interaction activity;
    computing a recommendation score for one or more wellness content items based on the user interaction data;
    ranking the one or more wellness content items based on the recommendation score to generate one or more recommended wellness content items; and
    transmitting a signal to cause a remote user device to output the one or more recommended wellness content items, with effect that the outputted one or more recommended wellness content items causes a positive emotional response in the user.

5. The method of claim 4, further comprising:
    receiving a second indication of the user's emotional state; and
    updating the user interaction data, based on the second indication.

6. The method of claim 4, further comprising:
    obtaining historical user interaction data for the user describing prior user interaction with one or more digital wellness content items; and
    updating the user interaction data, based on the historical user interaction data.

7. The method of claim 4, further comprising:
    outputting the user interaction data in a dashboard user interface.

8. The method of claim 4, wherein the one or more recommended wellness content items is one or more of:
    a cartoon or comic content item;
    a puzzle content item;
    a game content item;
    a quiz content item;
    a trivia content item;
    an artwork content item;
    a learning content item;
    a movement content item;
    an audio content item;
    a sleep training content item;
    an autonomous sensory meridian response (ASMR) content item;
    a microbreak content item; or
    a podcast content item.

9. An electronic device comprising:
    a camera;
    a memory storing instructions; and
    a processing unit coupled to the memory;
    wherein the processing unit is configured to execute the instructions to cause the device to:
        access a first digital wellness content item corresponding to a QR code at a predetermined physical location, the first digital wellness content item being accessed by scanning the QR code using the camera;
        responsive to detecting user interaction activity associated with the first digital wellness content item, obtain a first indication of a user's emotional state and location data corresponding to the predetermined physical location of the QR code and associated with the user interaction activity; and
        output, via a user interface for interacting with digital wellness content, one or more recommended wellness content items that are associated with the user's emotional state, the one or more recommended wellness content items being ranked using a recommendation score that is computed based on user interaction data including the first indication and the location data, with effect that the outputted one or more recommended wellness content items causes a positive emotional response in the user.

10. The electronic device of claim 9, wherein the processing unit is configured to execute the instructions to further cause the device to:
obtain, via the user interface, a second indication of the user's emotional state; and
display, via the user interface, the one or more recommended wellness content items that are associated with the user's emotional state, the one or more recommended wellness content items being ranked using the recommendation score that is computed based also on the second indication.

11. A non-transitory computer readable medium having instructions encoded thereon, wherein the instructions, when executed by a processing unit of an electronic device, cause the device to:
access a first digital wellness content item corresponding to a QR code at a predetermined physical location, the first digital wellness content item being accessed by scanning the QR code using the camera;
responsive to detecting user interaction activity associated with the first digital wellness content item, obtain a first indication of a user's emotional state and location data corresponding to the predetermined physical location and associated with the user interaction activity; and
output, via a user interface for interacting with digital wellness content, one or more recommended wellness content items that are associated with the user's emotional state, the one or more recommended wellness content items being ranked using a recommendation score that is computed based on user interaction data including the first indication and the location data, with effect that the outputted one or more recommended wellness content items causes a positive emotional response in the user.

12. A content serving system comprising:
a wellness content server;
a memory storing instructions; and
a processing unit coupled to the memory;
wherein the processing unit is configured to execute the instructions to cause the system to:
receive an indication of user interaction activity associated with a first digital wellness content item corresponding to a QR code at a predetermined physical location and being accessed by a user by scanning the QR code using a camera associated with an electronic device;
generate user interaction data for the first digital wellness content item, based on the user interaction activity, the user interaction data including a first indication of a user's emotional state and location data corresponding to the predetermined physical location of the QR code and associated with the user interaction activity;
compute a recommendation score for one or more wellness content items based on the user interaction data;
rank the one or more wellness content items based on the recommendation score to generate one or more recommended wellness content items; and
transmit a signal to cause a remote user device to output the one or more recommended wellness content items, with effect that the outputted one or more recommended wellness content items causes a positive emotional response in the user.

13. The content serving system of claim 12, wherein the processing unit is configured to execute the instructions to further cause the system to:
receive a second indication of the user's emotional state; and
update the user interaction data, based on the second indication.

14. The content serving system of claim 12, wherein the processing unit is configured to execute the instructions to further cause the system to:
obtain historical user interaction data for the user describing prior user interaction with one or more digital wellness content items; and
update the user interaction data, based on the historical user interaction data.

15. The content serving system of claim 12, wherein the processing unit is configured to execute the instructions to further cause the system to:
output the user interaction data in a dashboard user interface.

16. The content serving system of claim 12, wherein the one or more recommended wellness content items is one or more of:
a cartoon or comic content item;
a puzzle content item;
a game content item;
a quiz content item;
a trivia content item;
an artwork content item;
a learning content item;
a movement content item;
an audio content item;
a sleep training content item;
an autonomous sensory meridian response (ASMR) content item;
a microbreak content item; or
a podcast content item.

17. The method of claim 1, wherein the location data represents a geolocation of the electronic device that corresponds to the predetermined physical location of the QR code.

18. The method of claim 1, wherein the one or more recommended wellness content items represent one or more targeted, location-specific wellness interventions.

19. The method of claim 1, wherein the one or more recommended wellness content items are organized and displayed in the user interface in a sequence representing a digital wellness workout routine.

20. The method of claim 1, further comprising:
generating a wellness measure, based on the user interaction data, for tracking changes in the user's emotional state over time.

* * * * *